US010138362B2

(12) United States Patent
Wang et al.

(10) Patent No.: US 10,138,362 B2
(45) Date of Patent: *Nov. 27, 2018

(54) ETHYLENE-BASED POLYMER COMPOSITION FOR FILMS WITH IMPROVED TOUGHNESS

(71) Applicant: Dow Global Technologies LLC, Midland, MI (US)

(72) Inventors: Jian Wang, Freeport, TX (US); Pradeep Jain, Lake Jackson, TX (US); Mehmet Demirors, Freeport, TX (US); Douglas S. Ginger, Freeport, TX (US); Anthony J. Castelluccio, Lake Jackson, TX (US); Mridula Kapur, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/311,391

(22) PCT Filed: Jun. 26, 2015

(86) PCT No.: PCT/US2015/037869
§ 371 (c)(1),
(2) Date: Nov. 15, 2016

(87) PCT Pub. No.: WO2015/200740
PCT Pub. Date: Dec. 30, 2015

(65) Prior Publication Data
US 2017/0081444 A1    Mar. 23, 2017

Related U.S. Application Data

(60) Provisional application No. 62/017,525, filed on Jun. 26, 2014.

(51) Int. Cl.
*C08F 210/16* (2006.01)
*C08L 23/08* (2006.01)
(Continued)

(52) U.S. Cl.
CPC .... *C08L 23/0815* (2013.01); *A61F 13/51401* (2013.01); *A61F 13/51458* (2013.01); *B32B 5/00* (2013.01); *B32B 5/02* (2013.01); *B32B 5/022* (2013.01); *B32B 7/00* (2013.01); *B32B 7/02* (2013.01); *B32B 27/06* (2013.01); *B32B 27/08* (2013.01); *B32B 27/12* (2013.01); *B32B 27/18* (2013.01); *B32B 27/20* (2013.01); *B32B 27/28* (2013.01); *B32B 27/30* (2013.01); *B32B 27/306* (2013.01); *B32B 27/308* (2013.01); *B32B 27/32* (2013.01); *B32B 27/325* (2013.01);
(Continued)

(58) Field of Classification Search
CPC .. C08F 210/16; C08F 4/64193; C08F 4/6555; C08F 2/06; C08F 2500/10; C08F 2500/12; C08F 2500/19; C08F 2500/11; C08F 2500/18; C08L 23/0815; C08L 23/0807; C08L 2314/02; C08L 2314/06; C08L 2205/025; B32B 5/00; B32B 5/02; B32B 5/022; B32B 7/00; B32B 7/02; B32B 27/06; B32B 27/18; B32B 27/20; B32B 27/28; B32B 27/30; B32B 27/306; B32B 27/308; B32B 27/32; B32B 27/325; B32B 2255/00; B32B 2255/02; B32B 2262/00; B32B 2262/02; B32B 2262/0253; B32B 2307/50; B32B 2307/514; B32B 2307/544; B32B 2307/718; B32B 2307/724; B32B 2307/726; C08J 5/18; C08J 2323/06
See application file for complete search history.

(56) References Cited

U.S. PATENT DOCUMENTS 4,612,300 A   9/1986  Coleman, III
5,677,383 A  10/1997  Chum et al.
(Continued)

FOREIGN PATENT DOCUMENTS

WO   98/21274    †  5/1998
WO   98/21276 A1    5/1998
(Continued)

OTHER PUBLICATIONS

Karjala et al., Detection of Low Levels of Long-Chain Branching in Polyolefins, Antec, 2008, pp. 887-891.
Monrabel et al, Crystallization Elution Fractionation and Thermal Gradient Interaction Chromatography Techniques Comparison, Macromol, Symp., 2012, vol. 312, pp. 115-139.
PCT/US2015/037869; International Search Report & Written Opinion dated Dec. 14, 2015.
PCT/US2015/037869; International Preliminary Report on Patentability dated Sep. 15, 2016.
(Continued)

*Primary Examiner* — Nathan M Nutter

(57) ABSTRACT

The invention provides a composition comprising a first composition, comprising at least one ethylene-based polymer, and wherein the first composition comprises a MWCDI value greater than 0.9, and a melt index ratio I10/I2 that meets the following equation: I10/I2≥7.0−1.2×log (I2). The invention also provides a process to form a composition comprising at least two ethylene-based polymers, said process comprising the following: polymerizing ethylene, and optionally at least one comonomer, in solution, in the presence of a catalyst system comprising a metal-ligand complex of Structure I, as described herein, to form a first ethylene-based polymer; and polymerizing ethylene, and optionally at least one comonomer, in the presence of a catalyst system comprising a Ziegler/Natta catalyst, to form a second ethylene-based polymer.

12 Claims, 4 Drawing Sheets

(51) Int. Cl.

| | | |
|---|---|---|
| *B32B 5/00* | (2006.01) | |
| *B32B 5/02* | (2006.01) | |
| *B32B 7/00* | (2006.01) | |
| *B32B 7/02* | (2006.01) | |
| *B32B 27/06* | (2006.01) | |
| *B32B 27/18* | (2006.01) | |
| *B32B 27/20* | (2006.01) | |
| *B32B 27/28* | (2006.01) | |
| *B32B 27/30* | (2006.01) | |
| *B32B 27/32* | (2006.01) | |
| *C08J 5/18* | (2006.01) | |
| *A61F 13/514* | (2006.01) | |
| *B32B 27/08* | (2006.01) | |
| *B32B 27/12* | (2006.01) | |
| *C08K 3/26* | (2006.01) | |
| *C08J 5/00* | (2006.01) | |
| *E01C 13/08* | (2006.01) | |

(52) U.S. Cl.
CPC ............... *C08F 210/16* (2013.01); *C08J 5/00* (2013.01); *C08J 5/18* (2013.01); *C08K 3/26* (2013.01); *C08L 23/0807* (2013.01); *E01C 13/08* (2013.01); *A61F 2013/51409* (2013.01); *B32B 2255/00* (2013.01); *B32B 2255/02* (2013.01); *B32B 2262/00* (2013.01); *B32B 2262/02* (2013.01); *B32B 2262/0253* (2013.01); *B32B 2270/00* (2013.01); *B32B 2307/50* (2013.01); *B32B 2307/514* (2013.01); *B32B 2307/544* (2013.01); *B32B 2307/718* (2013.01); *B32B 2307/724* (2013.01); *B32B 2307/726* (2013.01); *B32B 2555/00* (2013.01); *C08F 2500/11* (2013.01); *C08F 2500/12* (2013.01); *C08F 2500/18* (2013.01); *C08J 2323/06* (2013.01); *C08J 2323/08* (2013.01); *C08J 2423/08* (2013.01); *C08K 2003/265* (2013.01); *C08L 2203/12* (2013.01); *C08L 2205/025* (2013.01); *C08L 2205/16* (2013.01); *C08L 2314/02* (2013.01); *C08L 2314/06* (2013.01)

(56) References Cited

U.S. PATENT DOCUMENTS

| | | | |
|---|---|---|---|
| 5,844,045 A † | 12/1998 | Kolthammer | |
| 5,869,575 A | 2/1999 | Kolthammer et al. | |
| 5,977,251 A | 11/1999 | Kao et al. | |
| 6,111,023 A | 8/2000 | Chum et al. | |
| 6,448,341 B1 | 9/2002 | Kolthammer et al. | |
| 6,545,088 B1 | 4/2003 | Kolthammer et al. | |
| 6,566,446 B1 | 5/2003 | Parikh et al. | |
| 6,908,968 B2 † | 6/2005 | Jain | |
| 2013/0046061 A1 | 2/2013 | Hermel-Davidock et al. | |
| 2013/0210990 A1 | 8/2013 | Demirors et al. | |
| 2014/0179873 A1 | 6/2014 | Lam et al. | |
| 2014/0242304 A1 | 8/2014 | Sandkuehler et al. | |
| 2014/0248811 A1 | 9/2014 | Degroot et al. | |
| 2015/0259586 A1* | 9/2015 | Kapur et al. | C08F 210/16 428/476.9 |
| 2017/0129229 A1* | 5/2017 | Wang et al. | B32B 27/32 |
| 2017/0129230 A1* | 5/2017 | Wang et al. | C08L 23/0815 |
| 2017/0152377 A1* | 6/2017 | Wang et al. | C08L 23/0815 |
| 2017/0226332 A1* | 8/2017 | Wang et al. | C08L 23/0815 |

FOREIGN PATENT DOCUMENTS

| | | | |
|---|---|---|---|
| WO | 1998021274 A1 | 5/1998 | |
| WO | 98/26000 A1 | 6/1998 | |
| WO | 2012/134700 † | 10/2012 | |
| WO | 2012134700 A2 | 10/2012 | |
| WO | 2014/058639 † | 4/2014 | |
| WO | 2014/058639 A1 | 4/2014 | |
| WO | 2015/198138 A1 | 12/2015 | |
| WO | 2015200741 A1 | 12/2015 | |
| WO | 2015200742 A1 | 12/2015 | |
| WO | 2015200743 A1 | 12/2015 | |

OTHER PUBLICATIONS

PCT/US2015/037869; Third Party Submission dated Apr. 15, 2016.
PCT/US2015/037869; Third Party Submission Summary dated Apr. 15, 2016.
Karjala et al., "Detection of Low Levels of Long-Chain Branching in Polyolefins", ANTEC, (2008), pp. 887-891.†
Monrabal et al., "Crystallization Elution Fractionation and Thermal Gradient Interaction Chromatography. Techniques Comparison", Macromol. Symp., vol. 312, (2012), pp. 115-129.†

\* cited by examiner
† cited by third party

ETHYLENE-BASED POLYMER COMPOSITION FOR FILMS WITH IMPROVED TOUGHNESS

REFERENCE TO RELATED APPLICATIONS

The present application claims the benefit of U.S. Provisional Application No. 62/017,525, filed Jun. 26, 2014, and incorporated herein by reference.

BACKGROUND OF THE INVENTION

Various polymerization techniques, using different catalyst systems, have been employed to produce ethylene-based polymer compositions suitable for films. Ethylene-based polymer compositions are described in the following references: U.S. Pat. No. 5,844,045 (see also U.S. Pat. No. 5,869,575 and U.S. Pat. No. 6,448,341), U.S. Pat. No. 6,566,446, U.S. Pat. No. 5,677,383 (see also U.S. Pat. No. 6,111,023), U.S. Pat. No. 5,977,251, US2015/0148490, US2015/0148491 and WO2014/058639. However, there remains a need for compositions that can be used to form films with improved toughness, while maintaining a good balance of other film physical properties, such as MD tear, puncture, and optics. These needs have been met by the following invention.

SUMMARY OF THE INVENTION

The instant invention provides a composition comprising a first composition, comprising at least one ethylene-based polymer, and wherein the first composition comprises a MWCDI value greater than 0.9, and a melt index ratio (I10/I2) that meets the following equation: $I10/I2 \geq 7.0 - 1.2 \times \log(I2)$.

The invention also provides a process to form a composition comprising at least two ethylene-based polymers, said process comprising the following:

polymerizing ethylene, and optionally at least one comonomer, in solution, in the presence of a catalyst system comprising a metal-ligand complex of Structure I, to form a first ethylene-based polymer; and polymerizing ethylene, and optionally at least one comonomer, in the presence of a catalyst system comprising a Ziegler/Natta catalyst, to form a second ethylene-based polymer; and wherein Structure I is as follows:

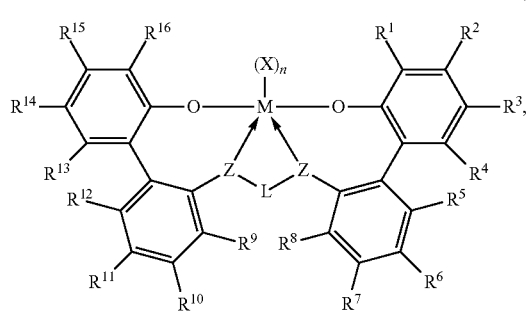

wherein:

M is titanium, zirconium, or hafnium, each independently being in a formal oxidation state of +2, +3, or +4; and n is an integer from 0 to 3, and wherein when n is 0, X is absent; and each X independently is a monodentate ligand that is neutral, monoanionic, or dianionic; or two Xs are taken together to form a bidentate ligand that is neutral, monoanionic, or dianionic; and X and n are chosen, in such a way, that the metal-ligand complex of formula (I) is, overall neutral; and each Z independently is O, S, $N(C_1-C_{40})$hydrocarbyl, or $P(C_1-C_{40})$hydrocarbyl; and wherein the Z-L-Z fragment is comprised of formula (1):

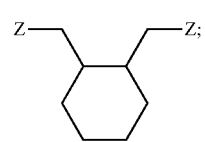

(1)

$R^1$ through $R^{16}$ are each, independently, selected from the group consisting of the following: a substituted or unsubstituted $(C_1-C_{40})$hydrocarbyl, a substituted or unsubstituted $(C_1-C_{40})$heterohydrocarbyl, $Si(R^C)_3$, $Ge(R^C)_3$, $P(R^P)_2$, $N(R^N)_2$, $OR^C$, $SR^C$, $NO_2$, $CN$, $CF_3$, $R^CS(O)-$, $R^CS(O)_2-$, $(R^C)_2C=N-$, $R^CC(O)O-$, $R^COC(O)-$, $R^CC(O)N(R)-$, $(R^C)_2NC(O)-$, halogen atom, hydrogen atom; and wherein each $R^C$ is independently a (C1-C30)hydrocarbyl; $R^P$ is a (C1-C30)hydrocarbyl; and $R^N$ is a (C1-C30)hydrocarbyl; and wherein, optionally, two or more R groups (from $R^1$ through $R^{16}$) can combine together into one or more ring structures, with such ring structures each, independently, having from 3 to 50 atoms in the ring, excluding any hydrogen atom.

DETAILED DESCRIPTION OF THE INVENTION

Figure 1:
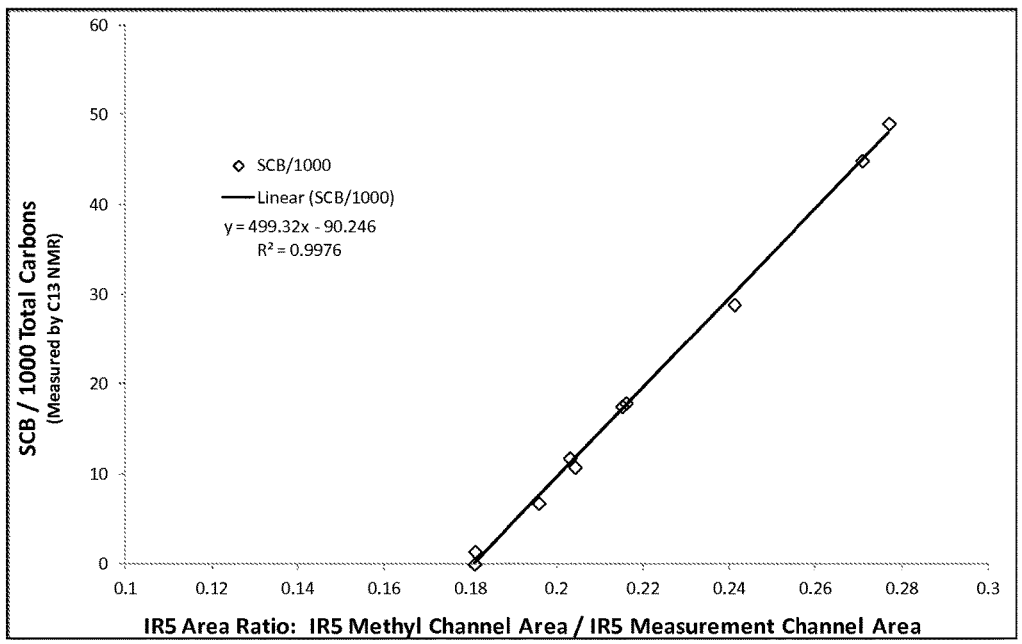
FIG. 1 depicts the plot of "$SCB_f$ versus IR5 Area Ratio" for ten SCB Standards.

It has been discovered that the inventive compositions can be used to form films with improved toughness. Such compositions contain an ethylene-based polymer that has a superior comonomer distribution, which is significantly higher in comonomer concentration, and a good distribution of comonomer, in the high molecular weight polymer molecules, and is significantly lower in comonomer concentration in the low molecular weight polymer molecules, as compared to conventional polymers of the art at the same overall density. It has also been discovered that the ethylene-based polymer has low LCB (Long Chain Branches), as indicated by low ZSVR, as compared to conventional polymers. As the result of this optimized distribution of the comonomer, as well as the inherent low LCB nature, the inventive compositions have more tie chains, and thus, improved film toughness.

As discussed above, the invention provides a composition comprising a first composition, comprising at least one ethylene-based polymer, and wherein the first composition comprises a MWCDI value greater than 0.9, and a melt index ratio (I10/I2) that meets the following equation: I10/I2≥7.0−1.2×log (I2).

The inventive composition may comprise a combination of two or more embodiments described herein.

The first composition may comprise a combination of two or more embodiments as described herein.

The ethylene-based polymer may comprise a combination of two or more embodiments as described herein.

In one embodiment, the first composition has a MWCDI value less than, or equal to, 10.0, further less than, or equal to, 8.0, further less than, or equal to, 6.0.

In one embodiment, the first composition has a MWCDI value less than, or equal to, 5.0, further less than, or equal to, 4.0, further less than, or equal to, 3.0.

In one embodiment, the first composition has a MWCDI value greater than, or equal to, 1.0, further greater than, or equal to, 1.1, further greater than, or equal to, 1.2.

In one embodiment, the first composition has a MWCDI value greater than, or equal to, 1.3, further greater than, or equal to, 1.4, further greater than, or equal to, 1.5.

In one embodiment, the first composition has a melt index ratio I10/I2 greater than, or equal to, 7.0, further greater than, or equal to, 7.1, further greater than, or equal to, 7.2, further greater than, or equal to, 7.3.

In one embodiment, the first composition has a melt index ratio I10/I2 less than, or equal to, 9.2, further less than, or equal to, 9.0, further less than, or equal to, 8.8, further less than, or equal to, 8.5.

In one embodiment, the first composition has a ZSVR value from 1.2 to 3.0, further from 1.2 to 2.5, further 1.2 to 2.0.

In one embodiment, the first composition has a vinyl unsaturation level greater than 10 vinyls per 1,000,000 total carbons. For example, greater than 20 vinyls per 1,000,000 total carbons, or greater than 50 vinyls per 1,000,000 total carbons, or greater than 70 vinyls per 1,000,000 total carbons, or greater than 100 vinyls per 1,000,000 total carbons.

In one embodiment, the first composition has a density in the range of 0.910 to 0.940 g/cm$^3$, for example from 0.910 to 0.930, or from 0.910 to 0.925 g/cm$^3$. For example, the density can be from a lower limit of 0.910, 0.912, or 0.914 g/cm$^3$, to an upper limit of 0.925, 0.927, or 0.930 g/cm$^3$ (1 cm$^3$=1 cc).

In one embodiment, the first composition has a melt index (I$_2$ or I2; at 190° C./2.16 kg) from 0.1 to 50 g/10 minutes, for example from 0.1 to 30 g/10 minutes, or from 0.1 to 20 g/10 minutes, or from 0.1 to 10 g/10 minutes. For example, the melt index (I$_2$ or I2; at 190° C./2.16 kg) can be from a lower limit of 0.1, 0.2, or 0.5 g/10 minutes, to an upper limit of 1.0, 2.0, 3.0, 4.0, 5.0, 10, 15, 20, 25, 30, 40, or 50 g/10 minutes.

In one embodiment, the first composition has a molecular weight distribution, expressed as the ratio of the weight average molecular weight to number average molecular weight ($M_w/M_n$; as determined by conv. GPC) in the range of from 2.2 to 5.0. For example, the molecular weight distribution ($M_w/M_n$) can be from a lower limit of 2.2, 2.3, 2.4, 2.5, 3.0, 3.2, or 3.4, to an upper limit of 3.9, 4.0, 4.1, 4.2, 4.5, 5.0.

In one embodiment, the first composition has a number average molecular weight ($M_n$; as determined by conv. GPC) in the range from 10,000 to 50,000 g/mole. For example, the number average molecular weight can be from a lower limit of 10,000, 20,000, or 25,000 g/mole, to an upper limit of 35,000, 40,000, 45,000, or 50,000 g/mole.

In one embodiment, the first composition has a weight average molecular weight ($M_w$; as determined by conv. GPC) in the range from 70,000 to 200,000 g/mole. For example, the number average molecular weight can be from a lower limit of 70,000, 75,000, or 78,000 g/mole, to an upper limit of 120,000, 140,000, 160,000, 180,000 or 200,000 g/mole.

In one embodiment, the first composition has a melt viscosity ratio, Eta*0.1/Eta*100, in the range from 2.2 to 7.0. For example, the number average molecular weight can be from a lower limit of 2.2, 2.3, 2.4 or 2.5, to an upper limit of 6.0, 6.2, 6.5, or 7.0.

In one embodiment, the ethylene-based polymer is an ethylene/α-olefin interpolymer, and further an ethylene/α-olefin copolymer.

In one embodiment, the first ethylene-based polymer is an ethylene/α-olefin interpolymer, and further an ethylene/α-olefin copolymer.

In one embodiment, the α-olefin has less than, or equal to, 20 carbon atoms. For example, the α-olefin comonomers may preferably have 3 to 10 carbon atoms, and more preferably 3 to 8 carbon atoms. Exemplary α-olefin comonomers include, but are not limited to, propylene, 1-butene, 1-pentene, 1-hexene, 1-heptene, 1-octene, 1-nonene, 1-decene, and 4-methyl-1-pentene. The one or more α-olefin comonomers may, for example, be selected from the group consisting of propylene, 1-butene, 1-hexene, and 1-octene; or in the alternative, from the group consisting of 1-butene, 1-hexene and 1-octene, and further 1-hexene and 1-octene.

In one embodiment, the ethylene-based polymer, or first ethylene-based polymer, has a molecular weight distribution ($M_w/M_n$; as determined by conv. GPC) in the range from 1.5 to 4.0, for example, from 1.5 to 3.5, or from 2.0 to 3.0. For example, the molecular weight distribution ($M_w/M_n$) can be from a lower limit of 1.5, 1.7, 2.0, 2.1, or 2.2, to an upper limit of 2.5, 2.6, 2.8, 3.0, 3.5 or 4.0.

In one embodiment, the first composition further comprises a second ethylene-based polymer. In a further embodiment, the second ethylene-based polymer is an ethylene/α-olefin interpolymer, and further an ethylene/α-olefin copolymer.

In one embodiment, the α-olefin has less than, or equal to, 20 carbon atoms. For example, the α-olefin comonomers may preferably have 3 to 10 carbon atoms, and more preferably 3 to 8 carbon atoms. Exemplary α-olefin comonomers include, but are not limited to, propylene, 1-butene, 1-pentene, 1-hexene, 1-heptene, 1-octene, 1-nonene, 1-decene, and 4-methyl-1-pentene. The one or more α-olefin comonomers may, for example, be selected from the group consisting of propylene, 1-butene, 1-hexene, and 1-octene; or in the alternative, from the group consisting of 1-butene, 1-hexene and 1-octene, and further 1-hexene and 1-octene.

In one embodiment, the second ethylene-based polymer is a heterogeneously branched ethylene/α-olefin interpolymer, and further a heterogeneously branched ethylene/α-olefin copolymer. Heterogeneously branched ethylene/α-olefin interpolymers and copolymers are typically produced using Ziegler/Natta type catalyst system, and have more comonomer distributed in the lower molecular weight molecules of the polymer.

In one embodiment, the second ethylene-based polymer has a molecular weight distribution ($M_w/M_n$) in the range from 3.0 to 5.0, for example from 3.2 to 4.6. For example, the molecular weight distribution ($M_w/M_n$) can be from a lower limit of 3.2, 3.3, 3.5, 3.7, or 3.9, to an upper limit of 4.6, 4.7, 4.8, 4.9, or 5.0.

In one embodiment, the composition comprises from 50 to 80 wt %, or from 50 to 85 wt %, or from 50 to 90 wt %, or from 50 to 95 wt % of the first composition, based on the weight of the composition.

In one embodiment, the composition comprises greater than, or equal to, 80 wt %, or greater than, or equal to, 85 wt %, or greater than, or equal to, 90 wt %, or greater than, or equal to, 95 wt %, or greater than, or equal to 98 wt % of the first composition, based on the weight of the composition.

In one embodiment, the composition further comprises another polymer. In a further embodiment, the polymer is selected from the following: a LLDPE, a MDPE, a LDPE, a HDPE, a propylene-based polymer, or a combination thereof.

In one embodiment, the composition further comprises a LDPE. In a further embodiment, the LDPE is present in an amount from 5 to 50 wt %, further from 10 to 40 wt %, further from 15 to 30 wt %, based on the weight of the composition. In a further embodiment, the LDPE has a density from 0.915 to 0.925 g/cc, and a melt index (I2) from 0.5 to 5 g/10 min, further from 1.0 to 3.0 g/10 min.

In one embodiment, the composition further comprises one or more additives. The invention also provides an article comprising at least one component formed from an inventive composition as described herein. In a further embodiment, the article is a film or a coating.

Polymerization

Polymerization processes include, but are not limited to, solution polymerization processes, using one or more conventional reactors, e.g., loop reactors, isothermal reactors, adiabatic reactors, stirred tank reactors, autoclave reactors in parallel, series, and/or any combinations thereof. The ethylene based polymer compositions may, for example, be produced via solution phase polymerization processes, using one or more loop reactors, adiabatic reactors, and combinations thereof.

In general, the solution phase polymerization process occurs in one or more well mixed reactors, such as one or more loop reactors and/or one or more adiabatic reactors at a temperature in the range from 115 to 250° C.; for example, from 135 to 200° C., and at pressures in the range of from 300 to 1000 psig, for example, from 450 to 750 psig.

In one embodiment, the ethylene based polymer composition (e.g., the first composition of claim 1) may be produced in two loop reactors in series configuration, the first reactor temperature is in the range from 115 to 200° C., for example, from 135 to 165° C., and the second reactor temperature is in the range from 150 to 210° C., for example, from 185 to 200° C. In another embodiment, the ethylene based polymer composition may be produced in a single reactor, the reactor temperature is in the range from 115 to 200° C., for example from 130 to 190° C. The residence time in a solution phase polymerization process is typically in the range from 2 to 40 minutes, for example from 5 to 20 minutes. Ethylene, solvent, one or more catalyst systems, optionally one or more cocatalysts, and optionally one or more comonomers, are fed continuously to one or more reactors. Exemplary solvents include, but are not limited to, isoparaffins. For example, such solvents are commercially available under the name ISOPAR E from ExxonMobil Chemical. The resultant mixture of the ethylene based polymer composition and solvent is then removed from the reactor or reactors, and the ethylene based polymer composition is isolated. Solvent is typically recovered via a solvent recovery unit, i.e., heat exchangers and separator vessel, and the solvent is then recycled back into the polymerization system.

In one embodiment, the ethylene based polymer composition may be produced, via a solution polymerization process, in a dual reactor system, for example a dual loop reactor system, wherein ethylene, and optionally one or more α-olefins, are polymerized in the presence of one or more catalyst systems, in one reactor, to produce a first ethylene-based polymer, and ethylene, and optionally one or more α-olefins, are polymerized in the presence of one or more catalyst systems, in a second reactor, to produce a second ethylene-based polymer. Additionally, one or more cocatalysts may be present.

In another embodiment, the ethylene based polymer composition may be produced via a solution polymerization process, in a single reactor system, for example, a single loop reactor system, wherein ethylene, and optionally one or more α-olefins, are polymerized in the presence of one or more catalyst systems. Additionally, one or more cocatalysts may be present.

As discussed above, the invention provides a process to form a composition comprising at least two ethylene-based polymers, said process comprising the following:

polymerizing ethylene, and optionally at least one comonomer, in solution, in the present of a catalyst system comprising a metal-ligand complex of Structure I, to form a first ethylene-based polymer; and polymerizing ethylene, and optionally at least one comonomer, in the presence of a catalyst system comprising a Ziegler/Natta catalyst, to form a second ethylene-based polymer; and wherein Structure I is as follows:

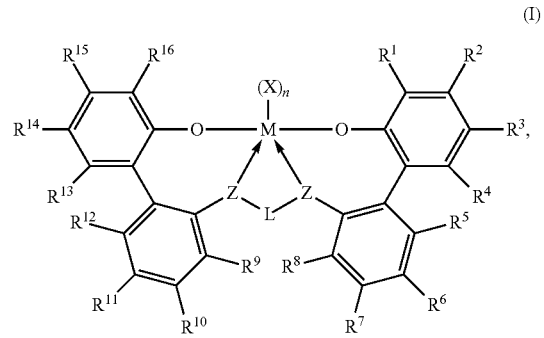

(I)

wherein:

M is titanium, zirconium, or hafnium, each, independently, being in a formal oxidation state of +2, +3, or +4; and n is an integer from 0 to 3, and wherein when n is 0, X is absent; and each X, independently, is a monodentate ligand that is neutral, monoanionic, or dianionic; or two Xs are taken together to form a bidentate ligand that is neutral, monoanionic, or dianionic; and X and n are chosen, in such a way, that the metal-ligand complex of formula (I) is, overall, neutral; and each Z, independently, is O, S, N(C$_1$-C$_{40}$)hydrocarbyl, or P(C$_1$-C$_{40}$)hydrocarbyl; and wherein the Z-L-Z fragment is comprised of formula (1):

(1)

R$^1$ through R$^{16}$ are each, independently, selected from the group consisting of the following: a substituted or unsubstituted (C$_1$-C$_{40}$)hydrocarbyl, a substituted or unsubstituted (C$_1$-C$_{40}$)heterohydrocarbyl, Si(R$^C$)$_3$, Ge(R$^C$)$_3$, P(R$^P$)$_2$, N(R$^N$)$_2$, OR$^C$, SR$^C$, NO$_2$, CN, CF$_3$, R$^C$S(O)—, R$^C$S(O)$_2$—, (R$^C$)$_2$C=N—, R$^C$C(O)O—, R$^C$OC(O)—, R$^C$C(O)N(R)—, (R$^C$)$_2$NC(O)—, halogen atom, hydrogen atom; and wherein each R$^C$ is independently a (C1-C30)hydrocarbyl; R$^P$ is a (C1-C30)hydrocarbyl; and R$^N$ is a (C1-C30)hydrocarbyl; and wherein, optionally, two or more R groups (from R$^1$ through R$^{16}$) can combine together into one or more ring structures, with such ring structures each, independently, having from 3 to 50 atoms in the ring, excluding any hydrogen atom.

An inventive process may comprise a combination of two or more embodiments as described herein.

In one embodiment, said process comprises polymerizing ethylene, and optionally at least one α-olefin, in solution, in the presence of a catalyst system comprising a metal-ligand complex of Structure I, to form a first ethylene-based polymer; and polymerizing ethylene, and optionally at least one α-olefin, in the presence of a catalyst system comprising a Ziegler/Natta catalyst, to form a second ethylene-based polymer. In a further embodiment, each α-olefin is independently a C1-C8 α-olefin.

In one embodiment, optionally, two or more R groups from R$^9$ through R$^{13}$, or R$^4$ through R$^8$ can combine together into one or more ring structures, with such ring structures each, independently, having from 3 to 50 atoms in the ring, excluding any hydrogen atom.

In one embodiment, M is hafnium.

In one embodiment, R$^3$ and R$^{14}$ are each independently an alkyl, and further a C1-C3 alkyl, and further methyl.

In one embodiment, R$^1$ and R$^{16}$ are each as follows:

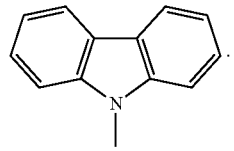

In one embodiment, each of the aryl, heteroaryl, hydrocarbyl, heterohydrocarbyl, Si(R$^C$)$_3$, Ge(R$^C$)$_3$, P(R$^P$)$_2$, N(R$^N$)$_2$, OR$^C$, SR$^C$, R$^C$S(O)—, R$^C$S(O)$_2$—, (R$^C$)$_2$C=N—, R$^C$C(O)O—, R$^C$OC(O)—, R$^C$C(O)N(R)—, (R$^C$)$_2$NC(O)—, hydrocarbylene, and heterohydrocarbylene groups, independently, is unsubstituted or substituted with one or more R$^S$ substituents; and each R$^S$ independently is a halogen atom, polyfluoro substitution, perfluoro substitution, unsubstituted (C$_1$-C$_{18}$)alkyl, F$_3$C—, FCH$_2$O—, F$_2$HCO—, F$_3$CO—, R$_3$Si—, R$_3$Ge—, RO—, RS—, RS(O)—, RS(O)$_2$—, R$_2$P—, R$_2$N—, R$_2$C=N—, NC—, RC(O)O—, ROC(O)—, RC(O)N(R)—, or R$_2$NC(O)—, or two of the R$^S$ are taken together to form an unsubstituted (C$_1$-C$_{18}$)alkylene, wherein each R independently is an unsubstituted (C$_1$-C$_{18}$)alkyl.

In one embodiment, two or more of R$^1$ through R$^{16}$ do not combine to form one or more ring structures.

In one embodiment, the catalyst system suitable for producing the first ethylene/α-olefin interpolymer is a catalyst system comprising bis((2-oxoyl-3-(dibenzo-1H-pyrrole-1-yl)-5-(methyl)phenyl)-2-phenoxymethyl)-methylene-1,2-cyclohexanediylhafnium (IV) dimethyl, represented by the following Structure: IA:

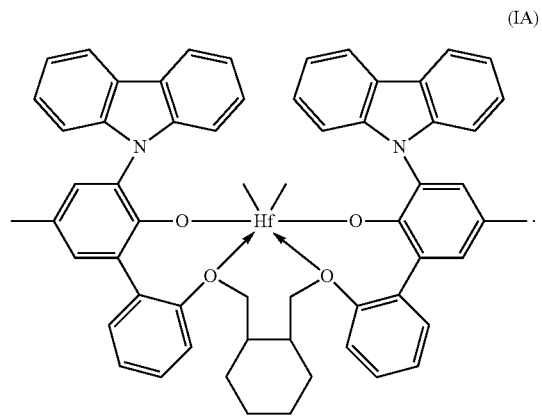

(IA)

The Ziegler/Natta catalysts suitable for use in the invention are typical supported, Ziegler-type catalysts, which are particularly useful at the high polymerization temperatures of the solution process. Examples of such compositions are those derived from organomagnesium compounds, alkyl halides or aluminum halides or hydrogen chloride, and a transition metal compound. Examples of such catalysts are described in U.S. Pat. Nos. 4,612,300; 4,314,912; and 4,547,475; the teachings of which are incorporated herein by reference.

Particularly suitable organomagnesium compounds include, for example, hydrocarbon soluble dihydrocarbylmagnesium, such as the magnesium dialkyls and the magnesium diaryls. Exemplary suitable magnesium dialkyls include, particularly, n-butyl-sec-butylmagnesium, diisopropylmagnesium, di-n-hexylmagnesium, isopropyl-n-butylmagnesium, ethyl-n-hexyl-magnesium, ethyl-n-butylmagnesium, di-n-octylmagnesium, and others, wherein the alkyl has from 1 to 20 carbon atoms. Exemplary suitable magnesium diaryls include diphenylmagnesium, dibenzylmagnesium and ditolylmagnesium. Suitable organomagnesium compounds include alkyl and aryl magnesium alkoxides and aryloxides and aryl and alkyl magnesium halides, with the halogen-free organomagnesium compounds being more desirable.

Halide sources include active non-metallic halides, metallic halides, and hydrogen chloride. Suitable non-metallic halides are represented by the formula R'X, wherein R' is hydrogen or an active monovalent organic radical, and X is a halogen. Particularly suitable non-metallic halides include, for example, hydrogen halides and active organic halides, such as t-alkyl halides, allyl halides, benzyl halides and other active hydrocarbyl halides. By an active organic halide is meant a hydrocarbyl halide that contains a labile halogen at least as active, i.e., as easily lost to another compound, as the halogen of sec-butyl chloride, preferably as active as t-butyl chloride. In addition to the organic monohalides, it is understood that organic dihalides, trihalides and other polyhalides that are active, as defined hereinbefore, are also suitably employed. Examples of preferred active non-metallic halides, include hydrogen chloride, hydrogen bromide, t-butyl chloride, t-amyl bromide, allyl chloride, benzyl chloride, crotyl chloride, methylvinyl carbinyl chloride, a-phenylethyl bromide, diphenyl methyl chloride, and the like. Most preferred are hydrogen chloride, t-butyl chloride, allyl chloride and benzyl chloride.

Suitable metallic halides include those represented by the formula MRy-a Xa, wherein: M is a metal of Groups IIB, IIIA or IVA of Mendeleev's periodic Table of Elements; R is a monovalent organic radical; X is a halogen; y has a value corresponding to the valence of M; and "a" has a value from 1 to y. Preferred metallic halides are aluminum halides of the formula $AlR_{3-a}$, $X_a$, wherein each R is independently hydrocarbyl, such as alkyl; X is a halogen; and a is a number from 1 to 3. Most preferred are alkylaluminum halides, such as ethylaluminum sesquichloride, diethylaluminum chloride, ethylaluminum dichloride, and diethylaluminum bromide, with ethylaluminum dichloride being especially preferred. Alternatively, a metal halide, such as aluminum trichloride, or a combination of aluminum trichloride with an alkyl aluminum halide, or a trialkyl aluminum compound may be suitably employed.

Any of the conventional Ziegler-Natta transition metal compounds can be usefully employed, as the transition metal component in preparing the supported catalyst component. Typically, the transition metal component is a compound of a Group IVB, VB, or VIB metal. The transition metal component is generally, represented by the formulas: $TrX'_{4-q}(OR1)q$, $TrX'_{4-q}(R2)q$, $VOX'_3$ and $VO(OR)_3$.

Tr is a Group IVB, VB, or VIB metal, preferably a Group IVB or VB metal, preferably titanium, vanadium or zirconium; q is 0 or a number equal to, or less than, 4; X' is a halogen, and R1 is an alkyl group, aryl group or cycloalkyl group having from 1 to 20 carbon atoms; and R2 is an alkyl group, aryl group, aralkyl group, substituted aralkyls, and the like.

The aryl, aralkyls and substituted aralkys contain 1 to 20 carbon atoms, preferably 1 to 10 carbon atoms. When the transition metal compound contains a hydrocarbyl group, R2, being an alkyl, cycloalkyl, aryl, or aralkyl group, the hydrocarbyl group will preferably not contain an H atom in the position beta to the metal carbon bond. Illustrative, but non-limiting, examples of aralkyl groups are methyl, neopentyl, 2,2-dimethylbutyl, 2,2-dimethylhexyl; aryl groups such as benzyl; cycloalkyl groups such as 1-norbornyl. Mixtures of these transition metal compounds can be employed if desired.

Illustrative examples of the transition metal compounds include $TiCl_4$, $TiBr_4$, $Ti(OC_2H_5)_3Cl$, $Ti(OC_2H_5)Cl_3$, $Ti(OC_4H_9)_3Cl$, $Ti(OC_3H_7)_2Cl_2$, $Ti(OC_6H_{13})_2Cl_2$, $Ti(OC_8H_{17})_2Br_2$, and $Ti(OC_{12}H_{25})Cl_3$, $Ti(O-iC_3H_7)_4$, and $Ti(O-nC_4H_9)_4$. Illustrative examples of vanadium compounds include $VCl_4$, $VOCl_3$, $VO(OC_2H_5)_3$, and $VO(OC_4H_9)_3$. Illustrative examples of zirconium compounds include $ZrCl_4$, $ZrCl_3(OC_2H_5)$, $ZrCl_2(OC_2H_5)_2$, $ZrCl(OC_2H_5)_3$, $Zr(OC_2H_5)_4$, $ZrCl_3(OC_4H_9)$, $ZrCl_2(OC_4H_9)_2$, and $ZrCl(OC_4H_9)3$.

An inorganic oxide support may be used in the preparation of the catalyst, and the support may be any particulate oxide, or mixed oxide which has been thermally or chemically dehydrated, such that it is substantially free of adsorbed moisture. See U.S. Pat. Nos. 4,612,300; 4,314,912; and 4,547,475; the teachings of which are incorporated herein by reference.

In one embodiment, the composition comprises a MWCDI value greater than 0.9. In one embodiment, the composition comprises a melt index ratio (I10/I2) that meets the following equation: I10/I2≥7.0−1.2×log (I2).

The composition may comprise one embodiment, or a combination of two or more embodiments, as listed above for the "first composition."

An inventive process may comprise a combination of two or more embodiments described herein.

Co-Catalyst Component

The above described catalyst systems can be rendered catalytically active by contacting it to, or combining it with, the activating co-catalyst, or by using an activating technique, such as those known in the art, for use with metal-based olefin polymerization reactions. Suitable activating co-catalysts, for use herein, include alkyl aluminums; polymeric or oligomeric alumoxanes (also known as aluminoxanes); neutral Lewis acids; and non-polymeric, non-coordinating, ion-forming compounds (including the use of such compounds under oxidizing conditions). A suitable activating technique is bulk electrolysis. Combinations of one or more of the foregoing activating co-catalysts and techniques are also contemplated. The term "alkyl aluminum" means a monoalkyl aluminum dihydride or monoalkylaluminum dihalide, a dialkyl aluminum hydride or dialkyl aluminum halide, or a trialkylaluminum. Aluminoxanes and their preparations are known at, for example, U.S. Pat. No. 6,103,657. Examples of preferred polymeric or oligomeric alumoxanes are methylalumoxane, triisobutylaluminum-modified methylalumoxane, and isobutylalumoxane.

Exemplary Lewis acid activating co-catalysts are Group 13 metal compounds containing from 1 to 3 hydrocarbyl substituents as described herein. In some embodiments, exemplary Group 13 metal compounds are tri(hydrocarbyl)-substituted-aluminum or tri(hydrocarbyl)-boron compounds. In some other embodiments, exemplary Group 13 metal compounds are tri(hydrocarbyl)-substituted-aluminum or tri(hydrocarbyl)-boron compounds are tri($(C_1$-$C_{10})$ alkyl)aluminum or tri($(C_6$-$C_{18})$aryl)boron compounds and halogenated (including perhalogenated) derivatives thereof. In some other embodiments, exemplary Group 13 metal compounds are tris(fluoro-substituted phenyl)boranes, in other embodiments, tris(pentafluorophenyl)borane. In some embodiments, the activating co-catalyst is a tris($(C_1$-$C_{20})$ hydrocarbyl) borate (e.g., trityl tetrafluoroborate) or a tri ($(C_1$-$C_{20})$hydrocarbyl)ammonium tetra($(C_1$-$C_{20})$hydrocarbyl)borane (e.g., bis(octadecyl)methylammonium tetrakis (pentafluorophenyl)borane). As used herein, the term "ammonium" means a nitrogen cation that is a ($(C_1$-$C_{20})$ hydrocarbyl)$_4$N$^+$, a ($(C_1$-$C_{20})$hydrocarbyl)$_3$N(H)$^+$, a ($(C_1$-$C_{20})$hydrocarbyl)$_2$N(H)$_2^+$, ($(C_1$-$C_{20})$hydrocarbylN(H)$_3^+$, or N(H)$_4^+$, wherein each ($C_1$-$C_{20}$)hydrocarbyl may be the same or different.

Exemplary combinations of neutral Lewis acid activating co-catalysts include mixtures comprising a combination of a tri($(C_1$-$C_4)$alkyl)aluminum and a halogenated tri($(C_6$-$C_{18})$ aryl)boron compound, especially a tris(pentafluorophenyl) borane. Other exemplary embodiments are combinations of such neutral Lewis acid mixtures with a polymeric or oligomeric alumoxane, and combinations of a single neutral Lewis acid, especially tris(pentafluorophenyl)borane with a polymeric or oligomeric alumoxane. Exemplary embodiments ratios of numbers of moles of (metal-ligand complex):(tris(pentafluoro-phenylborane): (alumoxane) [e.g., (Group 4 metal-ligand complex):(tris(pentafluoro-phenylborane):(alumoxane)] are from 1:1:1 to 1:10:30, other exemplary embodiments are from 1:1:1.5 to 1:5:10.

Many activating co-catalysts and activating techniques have been previously taught, with respect to different metal-ligand complexes, in the following USPNs: U.S. Pat. No. 5,064,802; U.S. Pat. No. 5,153,157; U.S. Pat. No. 5,296,433; U.S. Pat. No. 5,321,106; U.S. Pat. No. 5,350,723; U.S. Pat. No. 5,425,872; U.S. Pat. No. 5,625,087; U.S. Pat. No. 5,721,185; U.S. Pat. No. 5,783,512; U.S. Pat. No. 5,883,204; U.S. Pat. No. 5,919,983; U.S. Pat. No. 6,696,379; and U.S. Pat. No. 7,163,907. Examples of suitable hydrocarbyloxides are disclosed in U.S. Pat. No. 5,296,433. Examples of suitable Bronsted acid salts for addition polymerization catalysts are disclosed in U.S. Pat. No. 5,064,802; U.S. Pat. No. 5,919,983; U.S. Pat. No. 5,783,512. Examples of suitable salts of a cationic oxidizing agent and a non-coordinating, compatible anion, as activating co-catalysts for addition polymerization catalysts, are disclosed in U.S. Pat. No. 5,321,106. Examples of suitable carbenium salts as activating co-catalysts for addition polymerization catalysts are disclosed in U.S. Pat. No. 5,350,723. Examples of suitable silylium salts, as activating co-catalysts for addition polymerization catalysts, are disclosed in U.S. Pat. No. 5,625,087. Examples of suitable complexes of alcohols, mercaptans, silanols, and oximes with tris(pentafluorophenyl)borane are disclosed in U.S. Pat. No. 5,296,433. Some of these catalysts are also described in a portion of U.S. Pat. No. 6,515,155 B1, beginning at column 50, at line 39, and going through column 56, at line 55, only the portion of which is incorporated by reference herein.

In some embodiments, the above described catalyst systems can be activated to form an active catalyst composition by combination with one or more cocatalyst, such as a cation forming cocatalyst, a strong Lewis acid, or a combination thereof. Suitable cocatalysts for use include polymeric or oligomeric aluminoxanes, especially methyl aluminoxane, as well as inert, compatible, noncoordinating, ion forming compounds. Exemplary suitable cocatalysts include, but are not limited to, modified methyl aluminoxane (MMAO), bis(hydrogenated tallow alkyl)methyl, tetrakis(pentafluorophenyl)borate(1-) amine, triethyl aluminum (TEA), and any combinations thereof.

In some embodiments, one or more of the foregoing activating co-catalysts are used in combination with each other. In one embodiment, a combination of a mixture of a tri(($C_1$-$C_4$)hydrocarbyl)aluminum, tri(($C_1$-$C_4$)hydrocarbyl) borane, or an ammonium borate with an oligomeric or polymeric alumoxane compound, can be used.

Additives, Additional Polymers and Applications

An inventive composition may comprise one or more additives. Additives include, but are not limited to, antistatic agents, color enhancers, dyes, lubricants, fillers (for example, $TiO_2$ or $CaCO_3$), opacifiers, nucleators, processing aids, pigments, primary anti-oxidants, secondary anti-oxidants, UV stabilizers, anti-blocks, slip agents, tackifiers, fire retardants, anti-microbial agents, odor reducer agents, anti-fungal agents, and combinations thereof. An inventive composition may comprise from about 0.001 to about 10 percent by the combined weight of such additives, based on the weight of the composition including such additives.

An inventive composition may further comprise one or more other polymers. For example one or more other ethylene-based polymers (such polymers differ in one or more properties from the ethylene-based polymer of the first composition and the second ethylene-based polymer; i.e., density, melt index, comonomer, Mn, Mw, and/or MWD), or one or more propylene-based polymers, or combinations thereof. Such compositions may be blended via any method, known to a person of ordinary skill in the art, including, but not limited to, dry blending, and melt blending via any suitable equipment, for example, an extruder.

The invention provides for an article comprising at least one component formed from an inventive composition. Articles includes, but are not limited to, film, sheets, coatings, and multilayer structures. Multilayer structures typically comprise one or more film layers or sheets comprising an inventive composition. The multilayer structure may further comprise one or more layers comprising one or more polyamides, one or more polyesters, one or more olefin-based polymers, and combinations thereof.

Other articles include, but are not limited to, consumer and industrial packaging applications, such as construction film, heavy duty shipping sacks, protective film, waste management, and agricultural films, which require a film with high dart, puncture and/or tear resistance properties.

In one embodiment, the inventive compositions according to the present invention are characterized by one or more of the followings: (a) having a Dart impact A of at least 400 g, measured according to ASTM D1709 (Method A), when said composition is formed into a monolayer blown film having a thickness of 1 mil; and/or (b) having a normalized machine direction Elmendorf tear of at least 250 g/mil, measured according to ASTM D1922, when said polyolefin composition is formed into a monolayer blown film having a thickness of 1 mil.

In one embodiment, an inventive composition further comprises from 5 to 20 percent by weight of low density polyethylene (LDPE). In a further embodiment, the composition has a Dart Impact A greater than 275 g, preferably greater than 300 g, measured according to ASTM D1709, when said composition is formed into a monolayer blown film having a thickness of 1 mil.

DEFINITIONS

Unless stated to the contrary, implicit from the context, or customary in the art, all parts and percents are based on weight, and all test methods are current as of the filing date of this disclosure.

The term "composition," as used herein, includes material(s) which comprise the composition, as well as reaction products and decomposition products formed from the materials of the composition.

The term "comprising," and derivatives thereof, is not intended to exclude the presence of any additional component, step or procedure, whether or not the same is disclosed herein. In order to avoid any doubt, all compositions claimed, herein, through use of the term "comprising" may include any additional additive, adjuvant, or compound, whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed.

The term "polymer," as used herein, refers to a polymeric compound prepared by polymerizing monomers, whether of the same or a different type. The generic term polymer thus embraces the term homopolymer (employed to refer to polymers prepared from only one type of monomer, with the understanding that trace amounts of impurities can be incorporated into the polymer structure), and the term interpolymer as defined hereinafter. Trace amounts of impurities may be incorporated into and/or within the polymer.

The term "interpolymer," as used herein, refers to a polymer prepared by the polymerization of at least two different types of monomers. The generic term interpolymer thus includes copolymers (employed to refer to polymers prepared from two different types of monomers), and polymers prepared from more than two different types of monomers.

The term, "olefin-based polymer," as used herein, refers to a polymer that comprises, in polymerized form, a majority amount of olefin monomer, for example ethylene or propylene (based on the weight of the polymer), and optionally may comprise at least one polymerized comonomer.

The term, "ethylene-based polymer," as used herein, refers to a polymer that comprises a majority amount of polymerized ethylene monomer (based on the total weight of the polymer), and optionally may comprise at least one polymerized comonomer.

The term, "ethylene/α-olefin interpolymer," as used herein, refers to an interpolymer that comprises, in polymerized form, a majority amount of ethylene monomer (based on the weight of the interpolymer), and at least one α-olefin.

The term, "ethylene/α-olefin copolymer," as used herein, refers to a copolymer that comprises, in polymerized form, a majority amount of ethylene monomer (based on the weight of the copolymer), and an α-olefin, as the only two monomer types.

The term "propylene-based polymer," as used herein, refers to a polymer that comprises, in polymerized form, a majority amount of propylene monomer (based on the total weight of the polymer) and optionally may comprise at least one polymerized comonomer.

Test Methods
Melt Index

Melt indices $I_2$ (or I2) and $I_{10}$ (or I10) were measured in accordance to ASTM D-1238 (method B) at 190° C. and at 2.16 kg and 10 kg load, respectively. Their values are reported in g/10 min.

Density

Samples for density measurement were prepared according to ASTM D4703. Measurements were made, according to ASTM D792, Method B, within one hour of sample pressing.

Dynamic Shear Rheology

Each sample was compression-molded into "3 mm thick× 25 mm diameter" circular plaque, at 177° C., for five minutes, under 10 MPa pressure, in air. The sample was then taken out of the press and placed on a counter top to cool.

Constant temperature, frequency sweep measurements were performed on an ARES strain controlled rheometer (TA Instruments), equipped with 25 mm parallel plates, under a nitrogen purge. For each measurement, the rheometer was thermally equilibrated, for at least 30 minutes, prior to zeroing the gap. The sample disk was placed on the plate, and allowed to melt for five minutes at 190° C. The plates were then closed to 2 mm, the sample trimmed, and then the test was started. The method had an additional five minute delay built in, to allow for temperature equilibrium. The experiments were performed at 190° C., over a frequency range from 0.1 to 100 rad/s, at five points per decade interval. The strain amplitude was constant at 10%. The stress response was analyzed in terms of amplitude and phase, from which the storage modulus (G'), loss modulus (G"), complex modulus (G*), dynamic viscosity (η* or Eta*), and tan δ (or tan delta) were calculated.

Melt Strength

Melt strength measurements were conducted on a Gottfert Rheotens 71.97 (Goettfert Inc.; Rock Hill, S.C.) attached to a Gottfert Rheotester 2000 capillary rheometer. A polymer melt was extruded through a capillary die with a flat entrance angle (180 degrees), with a capillary diameter of 2.0 mm, and an aspect ratio (capillary length/capillary diameter) of 15.

After equilibrating the samples at 190° C., for 10 minutes, the piston was run at a constant piston speed of 0.265 mm/second. The standard test temperature was 190° C. The sample (about 20 grams) was drawn uniaxially to a set of accelerating nips, located 100 mm below the die, with an acceleration of 2.4 mm/second². The tensile force was recorded, as a function of the take-up speed of the nip rolls. Melt strength was reported as the plateau force (cN) before the strand broke. The following conditions were used, in the melt strength measurements: plunger speed=0.265 mm/second; wheel acceleration=2.4 mm/s²; capillary diameter=2.0 mm; capillary length=30 mm; and barrel diameter=12 mm.

Conventional Gel Permeation Chromatography (Conv. GPC)

A GPC-IR high temperature chromatographic system from PolymerChar (Valencia, Spain), was equipped with a Precision Detectors (Amherst, Mass.), 2-angle laser light scattering detector Model 2040, an IR5 infra-red detector and a 4-capillary viscometer, both from PolymerChar. Data collection was performed using PolymerChar Instrument Control software and data collection interface. The system was equipped with an on-line, solvent degas device and pumping system from Agilent Technologies (Santa Clara, Calif.).

Injection temperature was controlled at 150 degrees Celsius. The columns used, were three, 10-micron "Mixed-B" columns from Polymer Laboratories (Shropshire, UK). The solvent used was 1,2,4-trichlorobenzene. The samples were prepared at a concentration of "0.1 grams of polymer in 50 milliliters of solvent." The chromatographic solvent and the sample preparation solvent each contained "200 ppm of butylated hydroxytoluene (BHT)." Both solvent sources were nitrogen sparged. Ethylene-based polymer samples were stirred gently at 160 degrees Celsius for three hours. The injection volume was "200 microliters,' and the flow rate was "1 milliliters/minute." The GPC column set was calibrated by running 21 "narrow molecular weight distribution" polystyrene standards. The molecular weight (MW) of the standards ranges from 580 to 8,400,000 g/mole, and the standards were contained in six "cocktail" mixtures. Each standard mixture had at least a decade of separation between individual molecular weights. The standard mixtures were purchased from Polymer Laboratories. The polystyrene standards were prepared at "0.025 g in 50 mL of solvent" for molecular weights equal to, or greater than, 1,000,000 g/mole, and at "0.050 g in 50 mL of solvent" for molecular weights less than 1,000,000 g/mole.

The polystyrene standards were dissolved at 80° C., with gentle agitation, for 30 minutes. The narrow standards mixtures were run first, and in order of decreasing "highest molecular weight component," to minimize degradation. The polystyrene standard peak molecular weights were converted to polyethylene molecular weight using Equation 1 (as described in Williams and Ward, *J. Polym. Sci., Polym. Letters,* 6, 621 (1968)):

$$\text{Mpolyethylene} = A \times (\text{Mpolystyrene})^B \quad \text{(Eqn. 1),}$$

where M is the molecular weight, A is equal to 0.4316 and B is equal to 1.0.

Number-average molecular weight (Mn(conv gpc)), weight average molecular weight (Mw-cony gpc), and z-average molecular weight (Mz(conv gpc)) were calculated according to Equations 2-4 below.

$$Mn(conv\ gpc) = \frac{\sum_{i=RV_{integration\ start}}^{i=RV_{integration\ end}} (IR_{measurement\ channel_i})}{\sum_{i=RV_{integration\ start}}^{i=RV_{integration\ end}} (IR_{measurement\ channel_i} / M_{PE_i})} \quad \text{(Eqn. 2)}$$

$$Mw(conv\ gpc) = \frac{\sum_{i=RV_{integration\ start}}^{i=RV_{integration\ end}} (M_{PE_i} / IR_{measurement\ channel_i})}{\sum_{i=RV_{integration\ start}}^{i=RV_{integration\ end}} (IR_{measurement\ channel_i})} \quad \text{(Eqn. 3)}$$

$$Mz(conv\ gpc) = \frac{\sum_{i=RV_{integration\ start}}^{i=RV_{integration\ end}} (M_{PE_i}^2 / IR_{measurement\ channel_i})}{\sum_{i=RV_{integration\ start}}^{i=RV_{integration\ end}} (M_{PE_i} / IR_{measurement\ channel_i})} \quad \text{(Eqn. 4)}$$

In Equations 2-4, the RV is column retention volume (linearly-spaced), collected at "1 point per second," the IR is the baseline-subtracted IR detector signal, in Volts, from the IR5 measurement channel of the GPC instrument, and $M_{PE}$ is the polyethylene-equivalent MW determined from Equation 1. Data calculation were performed using "GPC One software (version 2.013H)" from PolymerChar.

Creep Zero Shear Viscosity Measurement Method

Zero-shear viscosities were obtained via creep tests, which were conducted on an AR-G2 stress controlled rheometer (TA Instruments; New Castle, Del.), using "25-mm-diameter" parallel plates, at 190° C. The rheometer oven was set to test temperature for at least 30 minutes, prior to zeroing the fixtures. At the testing temperature, a compression molded sample disk was inserted between the plates, and allowed to come to equilibrium for five minutes. The upper plate was then lowered down to 50 µm (instrument setting) above the desired testing gap (1.5 mm). Any superfluous material was trimmed off, and the upper plate was lowered to the desired gap. Measurements were done under nitrogen purging, at a flow rate of 5 L/min. The default creep time was set for two hours. Each sample was compression-molded into a "2 mm thick×25 mm diameter" circular plaque, at 177° C., for five minutes, under 10 MPa pressure, in air. The sample was then taken out of the press and placed on a counter top to cool.

A constant low shear stress of 20 Pa was applied for all of the samples, to ensure that the steady state shear rate was low enough to be in the Newtonian region. The resulting steady state shear rates were in the range from $10^{-3}$ to $10^{-4}$ $s^{-1}$ for the samples in this study. Steady state was determined by taking a linear regression for all the data, in the last 10% time window of the plot of "log (J(t)) vs. log(t)," where J(t) was creep compliance and t was creep time. If the slope of the linear regression was greater than 0.97, steady state was considered to be reached, then the creep test was stopped. In all cases in this study, the slope meets the criterion within one hour. The steady state shear rate was determined from the slope of the linear regression of all of the data points, in the last 10% time window of the plot of "ε vs. t," where ε was strain. The zero-shear viscosity was determined from the ratio of the applied stress to the steady state shear rate.

In order to determine if the sample was degraded during the creep test, a small amplitude oscillatory shear test was conducted before, and after, the creep test, on the same specimen from 0.1 to 100 rad/s. The complex viscosity values of the two tests were compared. If the difference of the viscosity values, at 0.1 rad/s, was greater than 5%, the sample was considered to have degraded during the creep test, and the result was discarded.

Zero-Shear Viscosity Ratio (ZSVR) is defined as the ratio of the zero-shear viscosity (ZSV) of the branched polyethylene material to the ZSV of a linear polyethylene material (see ANTEC proceeding below) at the equivalent weight average molecular weight (Mw(conv gpc)), according to the following Equation 5:

$$ZSVR = \frac{\eta_{0B}}{\eta_{0L}} = \frac{\eta_{0B}}{2.29^{-15} M_{w(conv\cdot gpc)}^{3.65}}. \quad \text{(Eqn. 5)}$$

The ZSV value was obtained from creep test, at 190° C., via the method described above. The Mw(conv gpc) value was determined by the conventional GPC method (Equation 3), as discussed above. The correlation between ZSV of linear polyethylene and its Mw(conv gpc) was established based on a series of linear polyethylene reference materials. A description for the ZSV-Mw relationship can be found in the ANTEC proceeding: Karjala et al., *Detection of Low Levels of Long-chain Branching in Polyolefins*, Annual Technical Conference—Society of Plastics Engineers (2008), 66th 887-891.

$^1$H NMR Method

A stock solution (3.26 g) was added to "0.133 g of the polymer sample" in 10 mm NMR tube. The stock solution was a mixture of tetrachloroethane-$d_2$ (TCE) and perchloroethylene (50:50, w:w) with 0.001M $Cr^{3+}$. The solution in the tube was purged with $N_2$, for 5 minutes, to reduce the amount of oxygen. The capped sample tube was left at room temperature, overnight, to swell the polymer sample. The sample was dissolved at 110° C. with periodic vortex mixing. The samples were free of the additives that may contribute to unsaturation, for example, slip agents such as erucamide. Each $^1$H NMR analysis was run with a 10 mm cryoprobe, at 120° C., on Bruker AVANCE 400 MHz spectrometer.

Two experiments were run to get the unsaturation: the control and the double presaturation experiments. For the control experiment, the data was processed with an exponential window function with LB=1 Hz, and the baseline was corrected from 7 to −2 ppm. The signal from residual $^1$H of TCE was set to 100, and the integral $I_{total}$ from −0.5 to 3 ppm was used as the signal from whole polymer in the control experiment. The "number of $CH_2$ group, $NCH_2$," in the polymer was calculated as follows in Equation 1A:

$$NCH_2 = I_{total}/2 \quad \text{(Eqn. 1A).}$$

For the double presaturation experiment, the data was processed with an exponential window function with LB=1 Hz, and the baseline was corrected from about 6.6 to 4.5 ppm. The signal from residual $^1$H of TCE was set to 100, and the corresponding integrals for unsaturations ($I_{vinylene}$, $I_{trisubstituted}$, and $I_{vinylidene}$) were integrated. It is well known to use NMR spectroscopic methods for determining polyethylene unsaturation, for example, see Busico, V., et al., *Macromolecules*, 2005, 38, 6988. The number of unsaturation unit for vinylene, trisubstituted, vinyl and vinylidene were calculated as follows:

$$N_{vinylene}=I_{vinylene}/2 \quad \text{(Eqn. 2A)}$$

$$N_{trisubstituted}=I_{trisubstitute} \quad \text{(Eqn. 3A)}$$

$$N_{vinyl}=I_{vinyl}/2 \quad \text{(Eqn. 4A)}$$

$$N_{vinylidene}=I_{vinylidene}/2 \quad \text{(Eqn. 5A)}$$

The unsaturation units per 1,000 carbons, all polymer carbons including backbone carbons and branch carbons, were calculated as follows:

$$N_{vinylene}/1,000C=(N_{vinylene}/NCH_2)*1,000 \quad \text{(Eqn. 6A)}$$

$$N_{trisubstituted}/1,000C=(N_{trisubstituted}/NCH_2)*1,000 \quad \text{(Eqn. 7A)}$$

$$N_{vinyl}/1,000C=(N_{vinyl}/NCH_2)*1,000 \quad \text{(Eqn. 8A)}$$

$$N_{vinylidene}/1,000C=(N_{vinylidene}/NCH_2)*1,000 \quad \text{(Eqn. 9A)}$$

The chemical shift reference was set at 6.0 ppm for the $^1$H signal from residual proton from TCE-d2. The control was run with ZG pulse, NS=4, DS=12, SWH=10,000 Hz, AQ=1.64 s, D1=14 s. The double presaturation experiment was run with a modified pulse sequence, with O1P=1.354 ppm, O2P=0.960 ppm, PL9=57 db, PL21=70 db, NS=100, DS=4, SWH=10,000 Hz, AQ=1.64 s, D1=1 s (where D1 is the presaturation time), D13=13 s. Only the vinyl levels were reported in Table 2 below.

$^{13}$C NMR Method

Samples are prepared by adding approximately 3 g of a 50/50 mixture of tetra-chloroethane-d2/orthodichlorobenzene, containing 0.025 M Cr(AcAc)$_3$, to a "0.25 g polymer sample" in a 10 mm NMR tube. Oxygen is removed from the sample by purging the tube headspace with nitrogen. The samples are then dissolved, and homogenized, by heating the tube and its contents to 150° C., using a heating block and heat gun. Each dissolved sample is visually inspected to ensure homogeneity.

All data are collected using a Bruker 400 MHz spectrometer. The data is acquired using a 6 second pulse repetition delay, 90-degree flip angles, and inverse gated decoupling with a sample temperature of 120° C. All measurements are made on non-spinning samples in locked mode. Samples are allowed to thermally equilibrate for 7 minutes prior to data acquisition. The 13C NMR chemical shifts were internally referenced to the EEE triad at 30.0 ppm.

C13 NMR Comonomer Content: It is well known to use NMR spectroscopic methods for determining polymer composition. ASTM D 5017-96; J. C. Randall et al., in "NMR and Macromolecules" ACS Symposium series 247; J. C. Randall, Ed., Am. Chem. Soc., Washington, D.C., 1984, Ch. 9; and J. C. Randall in "Polymer Sequence Determination", Academic Press, New York (1977) provide general methods of polymer analysis by NMR spectroscopy.

Molecular Weighted Comonomer Distribution Index (MW-CDI)

A GPC-IR, high temperature chromatographic system from PolymerChar (Valencia, Spain) was equipped with a Precision Detectors' (Amherst, Mass.) 2-angle laser light scattering detector Model 2040, and an IR5 infra-red detector (GPC-IR) and a 4-capillary viscometer, both from PolymerChar. The "15-degree angle" of the light scattering detector was used for calculation purposes. Data collection was performed using PolymerChar Instrument Control software and data collection interface. The system was equipped with an on-line, solvent degas device and pumping system from Agilent Technologies (Santa Clara, Calif.).

Injection temperature was controlled at 150 degrees Celsius. The columns used, were four, 20-micron "Mixed-A" light scattering columns from Polymer Laboratories (Shropshire, UK). The solvent was 1,2,4-trichlorobenzene. The samples were prepared at a concentration of "0.1 grams of polymer in 50 milliliters of solvent." The chromatographic solvent and the sample preparation solvent each contained "200 ppm of butylated hydroxytoluene (BHT)." Both solvent sources were nitrogen sparged. Ethylene-based polymer samples were stirred gently, at 160 degrees Celsius, for three hours. The injection volume was "200 microliters," and the flow rate was "1 milliliters/minute."

Calibration of the GPC column set was performed with 21 "narrow molecular weight distribution" polystyrene standards, with molecular weights ranging from 580 to 8,400,000 g/mole. These standards were arranged in six "cocktail" mixtures, with at least a decade of separation between individual molecular weights. The standards were purchased from Polymer Laboratories (Shropshire UK). The polystyrene standards were prepared at "0.025 grams in 50 milliliters of solvent" for molecular weights equal to, or greater than, 1,000,000 g/mole, and at "0.050 grams in 50 milliliters of solvent" for molecular weights less than 1,000,000 g/mole. The polystyrene standards were dissolved at 80 degrees Celsius, with gentle agitation, for 30 minutes. The narrow standards mixtures were run first, and in order of decreasing "highest molecular weight component," to minimize degradation. The polystyrene standard peak molecular weights were converted to polyethylene molecular weights using Equation 1B (as described in Williams and Ward, J. Polym. Sci., Polym. Let., 6, 621 (1968)):

$$\text{Mpolyethylene}=A \times (\text{Mpolystyrene})^B \quad \text{(Eqn. 1B)}$$

where M is the molecular weight, A has a value of approximately 0.40 and B is equal to 1.0. The A value was adjusted between 0.385 and 0.425 (depending upon specific column-set efficiency), such that NBS 1475A (NIST) linear polyethylene weight-average molecular weight corresponded to 52,000 g/mole, as calculated by Equation 3B, below:

$$Mn(LALS\ gpc) = \frac{\sum_{i=RV_{integration\ start}}^{i=RV_{integration\ end}} (IR_{measurement\ channel_i})}{\sum_{i=RV_{integration\ start}}^{i=RV_{integration\ end}} (IR_{measurement\ channel_i}/M_{PEi})} \quad \text{(Eqn. 2B)}$$

$$Mw(LALS\ gpc) = \frac{\sum_{i=RV_{integration\ start}}^{i=RV_{integration\ end}} (M_{PE_i} / IR_{measurement\ channel_i})}{\sum_{i=RV_{integration\ start}}^{i=RV_{integration\ end}} (IR_{measurement\ channel_i})} \quad \text{(Eqn. 3B)}$$

In Equations 2B and 3B, RV is column retention volume (linearly-spaced), collected at "1 point per second." The IR is the baseline-subtracted IR detector signal, in Volts, from the measurement channel of the GPC instrument, and the $M_{PE}$ is the polyethylene-equivalent MW determined from Equation 1B. Data calculation were performed using "GPC One software (version 2.013H)" from PolymerChar.

A calibration for the IR5 detector ratios was performed using at least ten ethylene-based polymer standards (polyethylene homopolymer and ethylene/octene copolymers;

narrow molecular weight distribution and homogeneous comonomer distribution) of known short chain branching (SCB) frequency (measured by the $^{13}$C NMR Method, as discussed above), ranging from homopolymer (0 SCB/1000 total C) to approximately 50 SCB/1000 total C, where total C=carbons in backbone+carbons in branches. Each standard had a weight-average molecular weight from 36,000 g/mole to 126,000 g/mole, as determined by the GPC-LALS processing method described above. Each standard had a molecular weight distribution (Mw/Mn) from 2.0 to 2.5, as determined by the GPC-LALS processing method described above. Polymer properties for the SCB standards are shown in Table A.

TABLE A

"SCB" Standards

| Wt % Comonomer | IR5 Area ratio | SCB/1000 Total C | Mw | Mw/Mn |
|---|---|---|---|---|
| 23.1 | 0.2411 | 28.9 | 37,300 | 2.22 |
| 14.0 | 0.2152 | 17.5 | 36,000 | 2.19 |
| 0.0 | 0.1809 | 0.0 | 38,400 | 2.20 |
| 35.9 | 0.2708 | 44.9 | 42,200 | 2.18 |
| 5.4 | 0.1959 | 6.8 | 37,400 | 2.16 |
| 8.6 | 0.2043 | 10.8 | 36,800 | 2.20 |
| 39.2 | 0.2770 | 49.0 | 125,600 | 2.22 |
| 1.1 | 0.1810 | 1.4 | 107,000 | 2.09 |
| 14.3 | 0.2161 | 17.9 | 103,600 | 2.20 |
| 9.4 | 0.2031 | 11.8 | 103,200 | 2.26 |

The "IR5 Area Ratio (or "IR5$_{Methyl\ Channel\ Area}$/IR5$_{Measurement\ Channel\ Area}$")" of "the baseline-subtracted area response of the IR5 methyl channel sensor" to "the baseline-subtracted area response of IR5 measurement channel sensor" (standard filters and filter wheel as supplied by PolymerChar: Part Number IR5_FWM01 included as part of the GPC-IR instrument) was calculated for each of the "SCB" standards. A linear fit of the SCB frequency versus the "IR5 Area Ratio" was constructed in the form of the following Equation 4B:

$$SCB/1000\ total\ C = A_0 + [A_1 \times (IR5_{Methyl\ Channel\ Area}/IR5_{Measurement\ Channel\ Area})] \quad (\text{Eqn. 4B}),$$

where $A_0$ is the "SCB/1000 total C" intercept at an "IR5 Area Ratio" of zero, and $A_1$ is the slope of the "SCB/1000 total C" versus "IR5 Area Ratio," and represents the increase in the "SCB/1000 total C" as a function of "IR5 Area Ratio."

A series of "linear baseline-subtracted chromatographic heights" for the chromatogram generated by the "IR5 methyl channel sensor" was established as a function of column elution volume, to generate a baseline-corrected chromatogram (methyl channel). A series of "linear baseline-subtracted chromatographic heights" for the chromatogram generated by the "IR5 measurement channel" was established as a function of column elution volume, to generate a base-line-corrected chromatogram (measurement channel).

The "IR5 Height Ratio" of "the baseline-corrected chromatogram (methyl channel)" to "the baseline-corrected chromatogram (measurement channel)" was calculated at each column elution volume index (each equally-spaced index, representing 1 data point per second at 1 ml/min elution) across the sample integration bounds. The "IR5 Height Ratio" was multiplied by the coefficient $A_1$, and the coefficient $A_0$ was added to this result, to produce the predicted SCB frequency of the sample. The result was converted into mole percent comonomer, as follows in Equation 5B:

$$\text{Mole Percent Comonomer} = \{SCB_f / [SCB_f + ((1000 - SCB_f \cdot \text{Length of comonomer}/2)]\} \cdot 100 \quad (\text{Eqn. 5B}),$$

where "$SCB_f$" is the "SCB per 1000 total C" and the "Length of comonomer"=8 for octene, 6 for hexene, and so forth.

Each elution volume index was converted to a molecular weight value ($Mw_i$) using the method of Williams and Ward (described above; Eqn. 1B). The "Mole Percent Comonomer (y axis)" was plotted as a function of $Log(Mw_i)$, and the slope was calculated between $Mw_i$ of 15,000 and $Mw_i$ of 150,000 g/mole (end group corrections on chain ends were omitted for this calculation). An EXCEL linear regression was used to calculate the slope between, and including, $Mw_i$ from 15,000 to 150,000 g/mole. This slope is defined as the molecular weighted comonomer distribution index (MWCDI=Molecular Weighted Comonomer Distribution Index).

Representative Determination of MWCDI (Inventive First Composition 2)

A plot of the measured "SCB per 1000 total C ($=SCB_f$)" versus the observed "IR5 Area Ratio" of the SCB standards was generated (see FIG. 1), and the intercept ($A_0$) and slope ($A_1$) were determined. Here, $A_0=-90.246$ SCB/1000 total C; and $A_1=499.32$ SCB/1000 total C.

Figure 2:
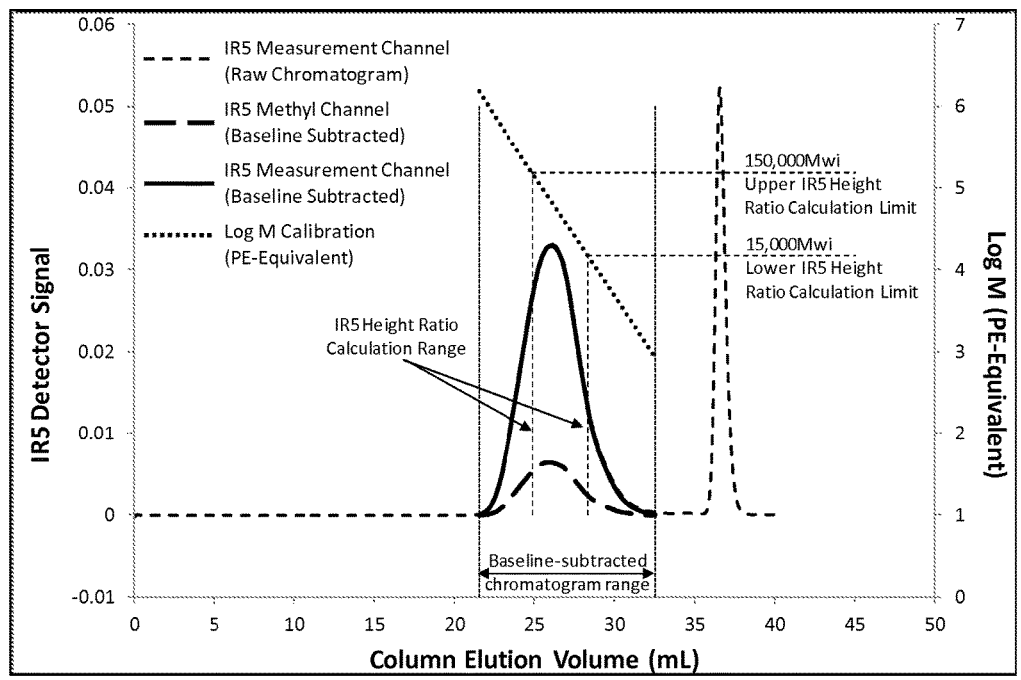
FIG. 2 depicts the several GPC profiles for the determination of IR5 Height Ratio for Inventive First Composition 2.
Figure 3:
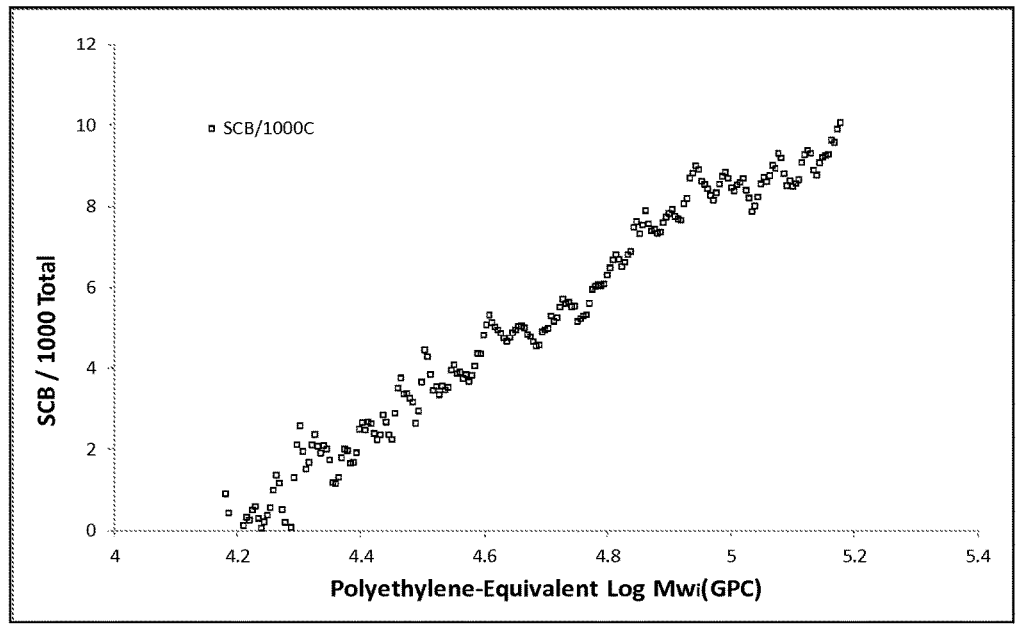
FIG. 3 depicts the plot of "$SCB_f$ versus Polyethylene Equivalent molecular Log $Mw_i$ (GPC)" for Inventive First Composition 2.

The "IR5 Height Ratio" was determined for Inventive Example 2 (see integration shown in FIG. 2). This height ratio (IR5 Height Ratio of Inventive Example 2) was multiplied by the coefficient $A_1$, and the coefficient $A_0$ was added to this result, to produce the predicted SCB frequency of this example, at each elution volume index, as described above ($A_0=-90.246$ SCB/1000 total C; and $A_1=499.32$ SCB/1000 total C). The $SCB_f$ was plotted as a function of polyethylene-equivalent molecular weight, as determined using Equation 1B, as discussed above. See FIG. 3 (Log Mwi used as the x-axis).

Figure 4:
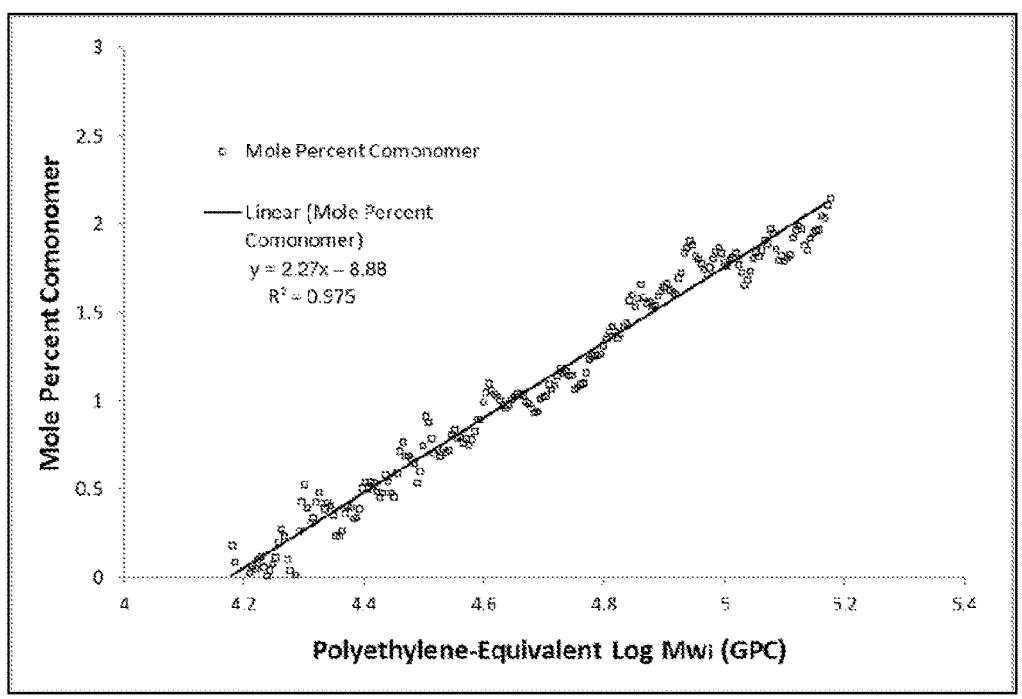
FIG. 4 depicts a plot of the "Mole Percent Comonomer versus Polyethylene Equivalent $Log_{Mwi}$ (GPC)" for Inventive First Composition 2.

The $SCB_f$ was converted into "Mole Percent Comonomer" via Equation 5B. The "Mole Percent Comonomer" was plotted as a function of polyethylene-equivalent molecular weight, as determined using Equation 1B, as discussed above. See FIG. 4 (Log Mwi used for the x-axis). A linear fit was from Mwi of 15,000 g/mole to Mwi of 150,000 g/mole, yielding a slope of "2.27 mole percent comonomer× mole/g." Thus, the MWCDI=2.27. An EXCEL linear regression was used to calculate the slope between, and including, Mwi from 15,000 to 150,000 g/mole.

Film Testing Conditions

The following physical properties were measured on the films produced (see experimental section).

45° Gloss: ASTM D-2457.

Clarity: ASTM: D-1746.

ASTM D1003 Total Haze

Samples measured for internal haze and overall (total) haze were sampled and prepared according to ASTM D1003. Internal haze was obtained via refractive index matching using mineral oil on both sides of the films. A Hazeguard Plus (BYK-Gardner USA; Columbia, Md.) was used for testing. Surface haze was determined as the difference between total haze and internal haze. The total haze was reported as the average of five measurements.

ASTM D1922 MD (Machine Direction) and CD (Cross Direction) Elmendorf Tear Type B The Elmendorf Tear test determines the average force to propagate tearing through a specified length of plastic film or non rigid sheeting, after the tear has been started, using an Elmendorf-type tearing tester.

After film production from the sample to be tested, the film was conditioned for at least 40 hours at 23° C. (+/−2°

C.) and 50% R.H (+/−5) as per ASTM standards. Standard testing conditions were 23° C. (+/−2° C.) and 50% R.H (+/−5) as per ASTM standards.

The force, in grams, required to propagate tearing across a film or sheeting specimen was measured, using a precisely calibrated pendulum device. In the test, acting by gravity, the pendulum swung through an arc, tearing the specimen from a precut slit. The specimen was held on one side by the pendulum, and on the other side by a stationary member. The loss in energy by the pendulum was indicated by a pointer or by an electronic scale. The scale indication was a function of the force required to tear the specimen.

The sample specimen geometry used in the Elmendorf tear test was the 'constant radius geometry,' as specified in ASTM D1922. Testing is typically carried out on specimens that have been cut from both the film MD and CD directions. Prior to testing, the film specimen thickness was measured at the sample center. A total of 15 specimens per film direction were tested, and the average tear strength and average thickness reported. The average tear strength was normalized to the average thickness.

ASTM D882 MD and CD, 1% and 2% Secant Modulus

The film MD (Machine Direction) and CD (Cross Direction) secant modulus was determined per ASTM D882. The reported secant modulus value was the average of five measurements.

Puncture Strength

The Puncture test determines the resistance of a film to the penetration of a probe, at a standard low rate, a single test velocity. The puncture test method is based on ASTM D5748. After film production, the film was conditioned for at least 40 hours at 23° C. (+/−2° C.) and 50% R.H (+/−5), as per ASTM standards. Standard testing conditions are 23° C. (+/−2° C.) and 50% R.H (+/−5) as per ASTM standards. Puncture was measured on a tensile testing machine. Square specimens were cut from a sheet, to a size of "6 inches by 6 inches." The specimen was clamped in a "4 inch diameter" circular specimen holder, and a puncture probe was pushed into the centre of the clamped film, at a cross head speed of 10 inches/minute. The internal test method follows ASTM D5748, with one modification. It deviated from the ASTM D5748 method, in that the probe used, was a "0.5 inch diameter" polished steel ball on a "0.25 inch" support rod (rather than the 0.75 inch diameter, pear shaped probe specified in D5748).

There was a "7.7 inch" maximum travel length to prevent damage to the test fixture. There was no gauge length; prior to testing, the probe was as close as possible to, but not touching the specimen. A single thickness measurement was made in the centre of the specimen. For each specimen, the maximum force, the force at break, the penetration distance, and the energy to break were determined. A total of five specimens were tested to determine an average puncture value. The puncture probe was cleaned using a "Kim-wipe" after each specimen.

ASTM D1709 Dart Drop

The film Dart Drop test determines the energy that causes a plastic film to fail, under specified conditions of impact by a free falling dart. The test result is the energy, expressed in terms of the weight of the missile falling from a specified height, which would result in the failure of 50% of the specimens tested.

After the film was produce, it was conditioned for at least 40 hours at 23° C. (+/−2° C.) and 50% R.H (+/−5), as per ASTM standards. Standard testing conditions are 23° C. (+/−2° C.) and 50% R.H (+/−5) as per ASTM standards.

The test result was reported as either by Method A, which uses a 1.5" diameter dart head and 26" drop height, or by Method B, which uses a 2" diameter dart head and 60" drop height. The sample thickness was measured at the sample center, and the sample then clamped by an annular specimen holder with an inside diameter of 5 inches. The dart was loaded above the center of the sample, and released by either a pneumatic or electromagnetic mechanism.

Testing was carried out according to the 'staircase' method. If the sample failed, a new sample was tested with the weight of the dart reduced by a known and fixed amount. If the sample did not fail, a new sample was tested with the weight of the dart increased by a known amount. After 20 specimens had been tested, the number of failures was determined. If this number was 10, then the test is complete. If the number was less than 10, then the testing continues, until 10 failures had been recorded. If the number was greater than 10, testing was continued, until the total of non-failures was 10. The Dart Drop strength was determined from these data, as per ASTM D1709, and expressed in grams, as either the Dart Drop impact of Type A or Type B. In some cases, the sample Dart Drop Impact strength may lie between A and B. In these cases, it is not possible to obtain a quantitative dart value.

EXPERIMENTAL

The following examples illustrate the present invention, but are not intended to limit the scope of the invention.

Inventive First Compositions 1, 2 and 3

Inventive first compositions 1, 2 and 3, each contain two ethylene-octene copolymers. Each composition was prepared, via solution polymerization, in a dual series loop reactor system according to U.S. Pat. No. 5,977,251 (see FIG. 2 of this patent), in the presence of a first catalyst system, as described below, in the first reactor, and a second catalyst system, as described below, in the second reactor.

The first catalyst system comprised a bis((2-oxoyl-3-(dibenzo-1H-pyrrole-1-yl)-5-(methyl)phenyl)-2-phenoxymethyl)-methylene-1,2-cyclohexanediylhafnium (IV) dimethyl, represented by the following formula (CAT 1):

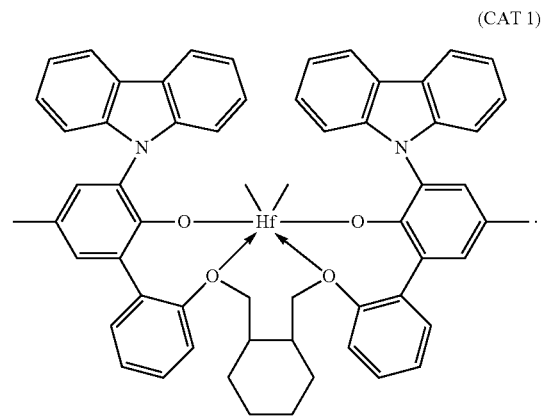

(CAT 1)

The molar ratios of the metal of CAT 1, added to the polymerization reactor, in-situ, to that of Cocat1 (modified methyl aluminoxane), or Cocat2 (bis(hydrogenated tallow alkyl)methyl, tetrakis(pentafluorophenyl)borate(1-)amine), are shown in Table 1.

The second catalyst system comprised a Ziegler-Natta type catalyst (CAT 2). The heterogeneous Ziegler-Natta type catalyst-premix was prepared substantially according to U.S. Pat. No. 4,612,300, by sequentially adding to a volume of ISOPAR E, a slurry of anhydrous magnesium chloride in ISOPAR E, a solution of $EtAlCl_2$ in heptane, and a solution of $Ti(O-iPr)_4$ in heptane, to yield a composition containing a magnesium concentration of 0.20M, and a ratio of Mg/Al/Ti of 40/12.5/3. An aliquot of this composition was further diluted with ISOPAR-E, to yield a final concentration of 500 ppm Ti in the slurry. While being fed to, and prior to entry into, the polymerization reactor, the catalyst premix was contacted with a dilute solution of $Et_3Al$, in the molar Al to Ti ratio specified in Table 1, to give the active catalyst.

Figure 5:
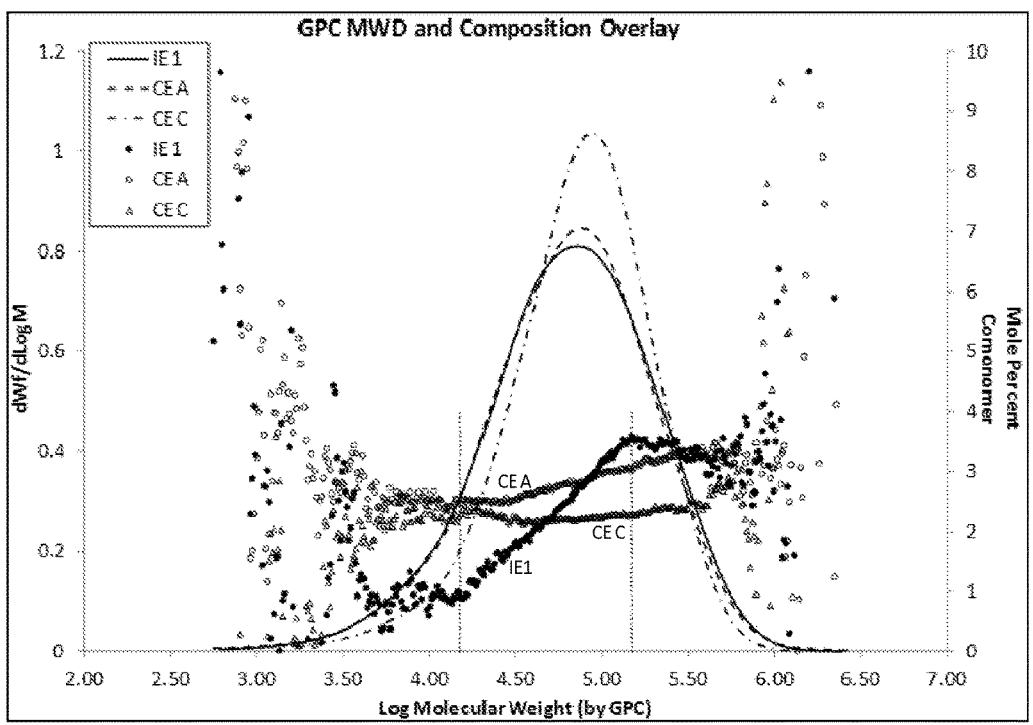
FIG. 5 depicts some GPC MWD profiles and corresponding comonomer distribution overlays for some inventive and comparative compositions (density 0.916-0.919 g/cc).
Figure 6:
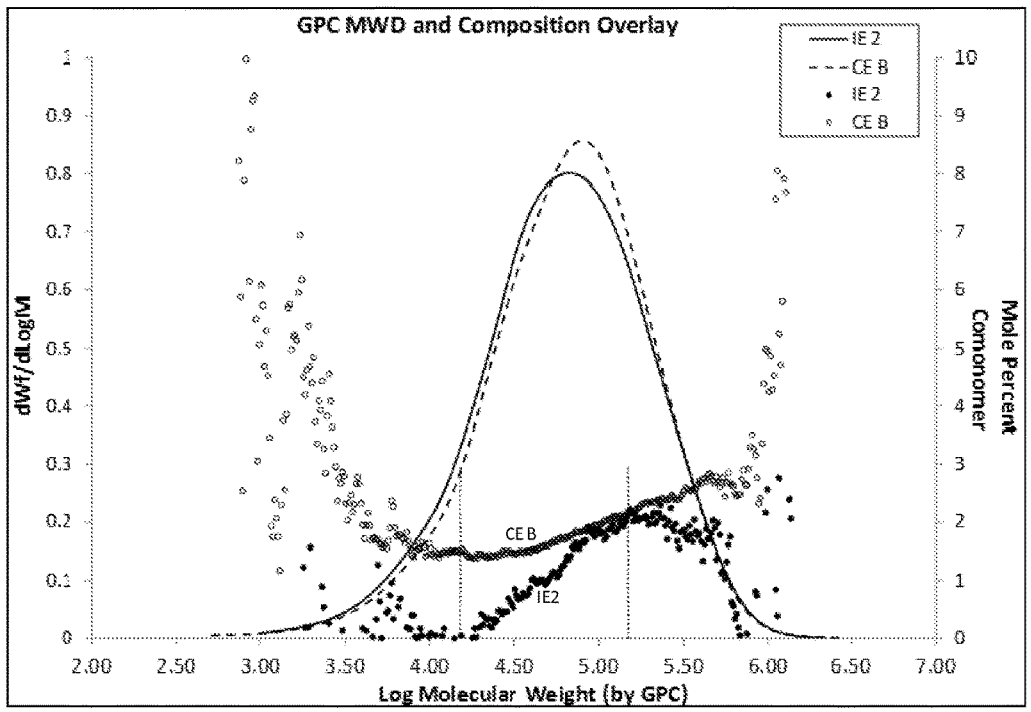
FIG. 6 depicts some GPC MWD profiles and corresponding comonomer distribution overlays for some inventive and comparative compositions (density 0.924-0.926 g/cc).
Figure 7:
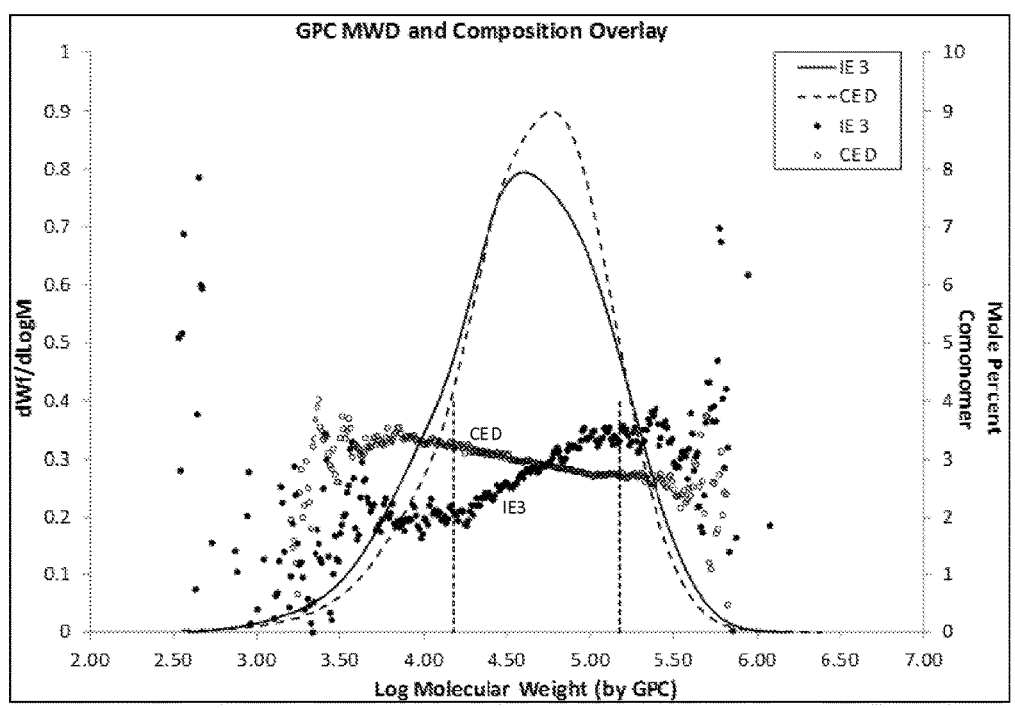
FIG. 7 depicts some GPC MWD profiles and corresponding comonomer distribution overlays for some inventive and comparative compositions (Cast stretch).

The polymerization conditions for the inventive first compositions 1, 2 and 3 are reported in Table 1. As seen in Table 1, Cocat. 1 (modified methyl aluminoxane (MMAO)); and Cocat. 2 (bis(hydrogenated tallow alkyl)methyl, tetrakis (pentafluorophenyl)borate(1-)amine) were each used as a cocatalyst for CAT 1. Additional properties of the inventive compositions 1, 2 and 3 were measured, and are reported in Table 2. The GPC MWD profiles, and corresponding comonomer distribution overlays, are shown in FIGS. 5-7. Each polymer composition was stabilized with minor (ppm) amounts of stabilizers.

Comparative First Compositions A and B

Comparative compositions A and B, each contain two ethylene-octene copolymers, and each was prepared, via solution polymerization, in a dual loop reactor system, in the presence of a first catalyst system, as described below, in the first reactor, and a second catalyst system, as described below, in the second reactor. The first catalyst system comprised titanium, [N-(1,1-dimethylethyl)-1,1-dimethyl-1-[(1,2,3,3a,8a-η)-1,5,6,7-tetrahydro-2-methyl-s-indacen-1-yl]silanaminato(2-)-κN][(1,2,3,4-η)-1,3-pentadiene]-(CAT 3, a constrained geometry catalyst). The second catalyst system comprised the Ziegler-Natta premix (CAT 2), as discussed above.

The polymerization conditions for comparative compositions A and B are reported in Table 1. As seen in Table 1, Cocat. 1 (modified methyl aluminoxane (MMAO)) and Cocat. 2 (bis(hydrogenated tallow alkyl)methyl, tetrakis (pentafluorophenyl)borate(1-)amine) were each used as cocatalyst for CAT 3. Additional properties of the comparative compositions A and B were measured, and are reported in Table 2. The GPC MWD profiles, and corresponding comonomer distribution overlays, are shown in FIGS. 5 and 6. Each polymer composition was stabilized with minor (ppm) amounts of stabilizers.

Comparative C (First Composition)

Comparative C is an ethylene-hexene copolymer composition, commercially available under the commercial designation EXCEED 1018CA from EXXONMOBIL Chemical Company, and having a density of approximately 0.918 $g/cm^3$, a melt index ($I_2$ or I2), measured at 190° C. and 2.16 kg, of approximately 1.0 g/10 minutes. Additional properties of the comparative example C were measured, and are reported in Table 2. The GPC MWD profile, and corresponding comonomer distribution overlay, is shown in FIG. 5.

Comparative D (First Composition)

Comparative D is an ethylene-octene copolymer composition, provided by The Dow Chemical Company, under the commercial designation ELITE 5230G, and having a density of approximately 0.916 $g/cm^3$, a melt index ($I_2$ or I2), measured at 190° C. and 2.16 kg, of approximately 4.0 g/10 minutes. Additional properties of the comparative example D were measured, and are reported in Table 2. The GPC MWD profile, and corresponding comonomer distribution overlay, is shown in FIG. 7.

TABLE 1

Polymerization Conditions (Rx1 = reactor 1; Rx2 = reactor 2)

| Sample # | Units | Inv. First 1 | Inv. First 2 | Inv. First 3 | Comp. First A | Comp. First B |
|---|---|---|---|---|---|---|
| Reactor Configuration | | Dual Series | Dual Series | Dual Series | Dual Series | Dual Series |
| Comonomer | | 1-octene | 1-octene | 1-octene | 1-octene | 1-octene |
| REACTOR FEEDS | | | | | | |
| Rx1 Total Solvent Flow | lb/hr | 1122 | 1057 | 1177 | 958 | 1061 |
| Rx1 Fresh Ethylene Flow | lb/hr | 181 | 167 | 260 | 176 | 178 |
| Rx1 Total Ethylene Flow | lb/hr | 190 | 175 | 269 | 184 | 187 |
| Rx1 Fresh Comonomer Flow | lb/hr | 42 | 29 | 61 | 29 | 28 |
| Rx1 Total Comonomer Flow | lb/hr | 74 | 48 | 118 | 97 | 58 |
| Rx1 Feed Solvent/Ethylene Ratio | Ratio | 6.19 | 6.32 | 4.52 | 5.44 | 5.96 |
| Rx1 Hydrogen Mole Percent | mol % | 0.55 | 0.44 | 1.29 | 0.04 | 0.07 |
| Rx1 Hydrogen Feed Flow | SCCM | 6827 | 5017 | 22848 | 525 | 857 |
| Rx2 Total Solvent Flow | lb/hr | 384 | 451 | 421 | 494 | 561 |
| Rx2 Fresh Ethylene Flow | lb/hr | 170 | 200 | 152 | 178 | 211 |
| Rx2 Total Ethylene Flow | lb/hr | 173 | 204 | 155 | 182 | 216 |
| Rx2 Fresh Comonomer Flow | lb/hr | 0 | 0 | 0 | 15 | 0 |
| Rx2 Total Comonomer Flow | lb/hr | 12 | 8 | 22 | 50 | 17 |
| Rx2 Hydrogen feed Flow | SCCM | 298 | 99 | 100 | 2446 | 3829 |
| Rx2 Feed Solvent/Ethylene Ratio | Ratio | 2.26 | 2.25 | 2.77 | 2.78 | 2.65 |
| Rx2 Hydrogen Mole Percent | mol % | 0.03 | 0.01 | 0.01 | 0.21 | 0.27 |
| REACTION | | | | | | |
| Rx1 Control Temperature | ° C. | 140 | 150 | 143 | 145 | 135 |
| Rx1 Ethylene Conversion | % | 86.7 | 90.5 | 72.7 | 69.4 | 77.7 |
| Rx1 FTnIR Exit C2 Conc. | g/L | 12.1 | 8.5 | 31.2 | 29.5 | 20.6 |
| Rx1 Viscosity | cP | 2400 | 2315 | 824 | 891 | 1318 |
| Rx2 Control Temperature | ° C. | 195 | 195 | 190 | 190 | 195 |
| Rx2 Ethylene Conversion | % | 87.1 | 86.0 | 87.8 | 89.2 | 88.8 |
| Rx2 FTnIR Exit C2 Conc | g/L | 8.3 | 9.9 | 8.5 | 8.6 | 8.6 |
| Rx2 Viscosity | cP | 869 | 876 | 264 | 892 | 848 |

TABLE 1-continued

Polymerization Conditions (Rx1 = reactor 1; Rx2 = reactor 2)

| Sample # | Units | Inv. First 1 | Inv. First 2 | Inv. First 3 | Comp. First A | Comp. First B |
|---|---|---|---|---|---|---|
| CATALYST | | | | | | |
| Rx1 Catalyst | | CAT 1 | CAT 1 | CAT 1 | CAT 3 | CAT 3 |
| Rx1 Catalyst Efficiency | g Polymer/g catalyst metal | 3,681,068 | 2,333,579 | 481,051 | 2,984,071 | 2,653,724 |
| Rx1 Cocat. 2 to Catalyst Metal Molar Ratio | Ratio | 1.3 | 1.8 | 1.2 | 1.2 | 1.5 |
| Rx1 Cocat. 1 to Catalyst Metal Molar Ratio | Ratio | 20 | 100 | 5 | 15 | 25 |
| Rx2 Catalyst Efficiency | g Polymer/g catalyst metal | 404,385 | 469,511 | 176,500 | 561,063 | 390,994 |
| Rx2 Al to Ti Molar Ratio | Ratio | 4.0 | 4.0 | 1.2 | 4.0 | 4.0 |

*solvent = ISOPAR E

TABLE 2

Properties of Inventive and Comparative Compositions

| | Unit | Inv. First 1 | Inv. First 2 | Inv. First 3 | Comp. First A | Comp. First B | Comp. First C | Comp. First D |
|---|---|---|---|---|---|---|---|---|
| Density | g/cc | 0.9174 | 0.9245 | 0.9148 | 0.9162 | 0.9253 | 0.9191 | 0.9158 |
| $I_2$ | g/10 min | 0.83 | 0.87 | 3.91 | 0.93 | 0.80 | 0.95 | 4.05 |
| $I_{10}/I_2$ | | 7.7 | 8.0 | 7.3 | 8.2 | 8.4 | 6.0 | 7.0 |
| $7.0 - 1.2 \times \log(I2)$ | | 7.1 | 7.1 | 6.3 | 7.0 | 7.1 | 7.0 | 6.3 |
| Mn (conv. gpc) | g/mol | 32,973 | 33,580 | 20,244 | 33,950 | 34,626 | 45,645 | 26,355 |
| Mw (conv. gpc) | | 117,553 | 117,172 | 78,820 | 111,621 | 112,688 | 109,931 | 76,118 |
| Mz (conv. gpc) | | 270,191 | 277,755 | 186,520 | 258,547 | 254,301 | 197,425 | 155,254 |
| Mw/Mn (conv. gpc) | | 3.57 | 3.49 | 3.89 | 3.29 | 3.25 | 2.41 | 2.89 |
| Mz/Mw (conv. gpc) | | 2.30 | 2.37 | 2.37 | 2.32 | 2.26 | 1.80 | 2.04 |
| Eta* (0.1 rad/s) | Pa · s | 9,496 | 11,231 | 1,997 | 10,342 | 11,929 | 6,975 | 2,057 |
| Eta* (1.0 rad/s) | Pa · s | 7,693 | 8,455 | 1,920 | 7,313 | 7,942 | 6,472 | 1,908 |
| Eta* (10 rad/s) | Pa · s | 4,706 | 4,977 | 1,527 | 4,337 | 4,586 | 5,071 | 1,473 |
| Eta* (100 rad/s) | Pa · s | 1,778 | 1,893 | 792 | 1,769 | 1,873 | 2,415 | 834 |
| Eta*0.1/Eta*100 | | 5.34 | 5.93 | 2.52 | 5.85 | 6.37 | 2.89 | 2.47 |
| Eta zero | Pa · s | 11,210 | 13,947 | 2,142 | 12,994 | 15,661 | 7,748 | 2,176 |
| Melt Strength | cN | 3.5 | 4.0 | NM | 3.9 | 4.5 | 3.0 | NM |
| MWCDI | | 2.64 | 2.27 | 1.56 | 0.65 | 0.79 | −0.06 | −0.54 |
| Vinyls | Per 1000 total Carbons | 134 | 179 | 115 | 157 | 148 | 69 | 56 |
| ZSVR | | 1.53 | 1.92 | 1.25 | 2.13 | 2.49 | 1.35 | 1.45 |

NM = Not Measured.

Monolayer Blown Films

Monolayer blown films were produced from the inventive compositions 1 and 2 and comparative compositions A, B and C, via an Egan Davis Standard extruder, equipped with a semi grooved barrel of ID 3.5 inch; 30/1 L/D ratio; a barrier screw, and an Alpine air ring. The extrusion line had an "8 inch die" with internal bubble cooling. The extrusion line also had a film thickness gauge scanner. The film fabrication conditions were as follows: film thickness maintained at 1 mil (0.001 in or 0.0254 mm); blow up ratio (BUR) 2.5; die gap 90 mil; and frost line height (FLH) 30 inch, at a output rate of approximately "10 lbs per inch" of circumference of the die, and an approximately 410 degree Fahrenheit polymer melt temperature. Film properties are reported in Table 3.

Inventive compositions 1 and 2 and Comparative compositions A, B and C were further dry blended with a low density polyethylene (LDPE) at 80:20 weight ratio (Expt. First Composition: LDPE), and the respective monolayer blown films were produced via an Egan Davis Standard extruder, equipped with a semi grooved barrel of ID 3.5 inch; 30/1 L/D ratio; a barrier screw, and an Alpine air ring. The extrusion line had an "8 inch die" with internal bubble cooling. The extrusion line also had a film thickness gauge scanner. The film fabrication conditions were as follows: film thickness maintained at 1 mil (0.001 in or 0.0254 mm); blow up ratio (BUR) 2.5; die gap 90 mil; and frost line height (FLH) 30 inch, at a output rate of approximately 10 lbs per inch of circumference of the die, and an approximately 410 degree Fahrenheit polymer melt temperature. The LDPE (AGILITY 1021 from The Dow Chemical Company) had melt index $I_2$ of 2 g/10 minutes, and density of 0.919 g/cm³. Film properties are reported in Table 3.

Monolayer Cast Films

Monolayer cast films of inventive composition 3 and comparative composition D were fabricated on a 5 layer, Egan Davis Standard coextrusion cast film line. Film thickness was maintained at 0.8 mil (0.0008 in or 0.02 mm). The cast line consisted of three 2½" and two 2" "30:1 L/D Egan Davis Standard MAC extruders," which are air cooled. All extruders had moderate work DSB (Davis Standard Barrier) type screws. A CMR 2000 microprocessor monitored and controlled the operations. The extrusion process was monitored by pressure transducers, located before, and after, the breaker plate, as well as by four heater zones on each barrel, one each at the adapter and the block and two zones on the die. The microprocessor also tracked the extruder RPM, % FLA, HP, rate, line speed, % draw, primary and secondary chill roll temperatures, gauge deviation, layer ratio, rate/RPM, and melt temperature for each extruder.

Equipment specifications included a Cloeren 5 layer, dual plane feed block, and a Cloeren 36" Epich II autogage 5.1 die. The primary chill roll had a matte finish, and was 40" O.D.×40" long, with a 30-40 RMS surface finish for improved release characteristics. The secondary chill roll is 20" O.D.×40" long, with a 2-4 RMS surface for improved web tracking. Both the primary and secondary chill rolls had chilled water circulating through them, to provide quenching. There was an NDC Beta gauge sensor for gauge thickness and automatic gauge control, if needed. Rate was measured by five Barron weigh hoppers, with load cells on each hopper for gravimetric control. Samples were finished on the two position, single turret Horizon winder, on 3" I.D. cores, with center wind automatic roll changeover and slitter station. The maximum throughput rate for the line was "600 pounds per hour," and maximum line speed was "900 feet per minute." Film properties are shown in Table 4.

Monolayer cast films for inventive composition 3 and comparative composition D were fabricated based on the following conditions:
Melt Temperature=530° F.
Temperature Profile (B1 300° F.:B2 475° F., B3-5 525° F., Screen 525° F., Adaptor 525° F., Die all zones 525° F.)
Line speed=470 ft/min
Through put rate=370-400 lb/hr
Chill roll temperature=70° F.
Cast roll temperature=70° F.
Air knife=7.4" $H_2O$
Vacuum box=OFF
Die gap=20-25 mil

TABLE 3

Blown Film Properties

|  |  | Inv. 1 | Inv. 2 | Comp. A | Comp. B | Comp. C |
|---|---|---|---|---|---|---|
| 100% Expt. First Composition |  |  |  |  |  |  |
| Dart Drop Impact (Method-A) | g | 1363 | 553 | 583 | 238 | 880 |
| Normalized tear (MD) | g/mil | 280 | 251 | 314 | 269 | 277 |
| Normalized tear (CD) | g/mil | 526 | 611 | 593 | 666 | 386 |
| Gloss - 45 degree | % | 39 | 35 | 52 | 37 | 44 |
| Haze - total | % | 19.4 | 18.7 | 13.2 | 21.0 | 12.7 |
| Puncture Strength | ft * lbf/in 3 | 362 | 310 | 419 | 252 | 416 |
| Secant Modulus - MD at 1% strain | psi | 35,612 | 45,023 | 30,013 | 51,238 | 31,178 |
| Secant Modulus - MD at 2% strain | psi | 32,243 | 39,572 | 26,818 | 43,100 | 26,890 |
| 80% Expt. First Composition + 20% LDPE |  |  |  |  |  |  |
| Dart Drop Impact (Method-A) | g | 494 | 176 | 200 | 143 | 241 |
| Normalized tear (MD) | g/mil | 135 | 115 | 141 | 116 | 115 |
| Normalized tear (CD) | g/mil | 739 | 821 | 692 | 759 | 645 |
| Gloss - 45 degree | % | 76 | 70 | 70 | 62 | 82 |
| Haze - total | % | 4.7 | 6.0 | 5.5 | 7.5 | 3.1 |
| Puncture Strength | ft * lbf/in 3 | 246 | 193 | 274 | 168 | 298 |
| Secant Modulus - MD at 1% strain | psi | 45,544 | 53,234 | 34,564 | 45,254 | 38,927 |
| Secant Modulus - MD at 2% strain | psi | 38,999 | 45,301 | 30,772 | 41,253 | 34,383 |

TABLE 4

Cast Film Properties

|  | Unit | Inv. 3 | Comp. D |
|---|---|---|---|
| Dart Drop Impact (Method-A) | g | 463 | 211 |
| Normalized tear (MD) | g/mil | 375 | 351 |
| Normalized tear (CD) | g/mil | 557 | 600 |
| Clarity | % | 99.5 | 99.6 |
| Puncture Strength | ft*lbf/in^3 | 225 | 352 |
| Secant Modulus - MD at 1% strain | psi | 14,676 | 14,803 |
| Secant Modulus - MD at 2% strain | psi | 13,232 | 13,732 |
| Secant Modulus - CD at 1% strain | psi | 14,479 | 15,084 |
| Secant Modulus - CD at 2% strain | psi | 13,654 | 13,829 |

It has been discovered, that for blown films, within the density range from 0.916 to 0.919 g/cc, inventive first composition 1 showed significantly higher toughness (as indicated by dart drop impact values) than comparative compositions A and C. Within the density range from 0.924 to 0.926 g/cc, inventive first composition 2 also showed significantly higher toughness (as indicated by dart drop impact values) than comparative composition B. It has also been discovered, that for the cast films, inventive example 3 showed significantly higher toughness (as indicated by dart drop impact values) than comparative composition D. It is believed that the improved film toughness from the inventive compositions is a result of their high MWCDI values. From a molecular structure standpoint, a high MWCDI value indicates comonomers are more favorably incorporated (a higher incorporation of comonomer and a better distribution of comonomer) in the high molecular weight polymer molecules, rather than in the low molecular weight polymer molecules. The inventive compositions also have low LCB, as indicated by low ZSVR, as compared to conventional polymers. As a result, the polymer contains more tie chains, and therefore, provides better film toughness. The inventive compositions also have significantly high I10/I2 values, indicating good processibility of these compositions.

The invention claimed is:

1. A composition comprising a first composition, comprising at least one ethylene-based polymer, and wherein the first composition comprises a MWCDI value greater than 1.2, and a melt index ratio (I10/I2) that meets the following equation: I10/I2≥7.0−1.2×log (I2).

2. The composition of claim 1, wherein the first composition has a MWCDI value less than, or equal to, 10.0.

3. The composition of claim 1, wherein the ethylene-based polymer is an ethylene/α-olefin interpolymer.

4. The composition of claim 1, wherein the first composition further comprises a second ethylene-based polymer.

5. The composition of claim 4, wherein the second ethylene-based polymer is an ethylene/α-olefin interpolymer.

6. The composition of claim 1, wherein the first composition has a ZSVR value from 1.2 to 3.0.

7. The composition of claim 1, wherein the first composition has a melt index ratio I10/I2 less than, or equal to, 9.2.

8. The composition of claim 1, wherein the first composition has a vinyl unsaturation level greater than 10 vinyls per 1,000,000 total carbons.

9. The composition of claim 1, wherein the composition further comprises another polymer.

10. The composition of claim 9, wherein the polymer is selected from the following: a LLDPE, a LDPE, a HDPE, a propylene-based polymer, or a combination thereof.

11. An article comprising at least one component formed from the composition of claim 1.

12. The article of claim 11, wherein the article is a film or coating.

* * * * *